(12) United States Patent
de Medina et al.

(10) Patent No.: US 10,188,666 B2
(45) Date of Patent: Jan. 29, 2019

(54) DENDROGENIN A AND ANTINEOPLASTIC AGENTS FOR THE TREATMENT OF CHEMOSENSITIVE OR CHEMORESISTANT TUMORS

(71) Applicants: Affichem, Toulouse (FR); INSERM (Institut National de la Sante et de la Recherche Medicale), Paris (FR)

(72) Inventors: Philippe de Medina, Toulouse (FR); Michael Paillasse, Toulouse (FR); Christian Recher, Toulouse (FR); Marc Poirot, Toulouse (FR); Sandrine Silvente Poirot, Toulouse (FR)

(73) Assignees: AFFICHEM, Toulouse (FR); INSERM (INSTITUT NATIONAL DE LA SANTE ET DE LA RECHERCHE MEDICALE), Paris (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 0 days.

(21) Appl. No.: 14/915,790

(22) PCT Filed: Sep. 3, 2014

(86) PCT No.: PCT/EP2014/068772
§ 371 (c)(1),
(2) Date: Mar. 1, 2016

(87) PCT Pub. No.: WO2015/032838
PCT Pub. Date: Mar. 12, 2015

(65) Prior Publication Data
US 2016/0193233 A1    Jul. 7, 2016

(30) Foreign Application Priority Data
Sep. 4, 2013 (EP) .................................. 13306206

(51) Int. Cl.
*A61K 31/58*  (2006.01)
*A61K 31/575* (2006.01)
*A61K 31/704* (2006.01)
*A61K 33/24*  (2006.01)
*A61K 33/36*  (2006.01)
*A61K 45/06*  (2006.01)

(52) U.S. Cl.
CPC ............ *A61K 31/58* (2013.01); *A61K 31/575* (2013.01); *A61K 31/704* (2013.01); *A61K 33/24* (2013.01); *A61K 33/36* (2013.01); *A61K 45/06* (2013.01)

(58) Field of Classification Search
CPC .... A61K 31/58; A61K 31/575; A61K 31/704; A61K 33/24; A61K 33/36; A61K 45/06
See application file for complete search history.

(56) References Cited

U.S. PATENT DOCUMENTS

2006/0111358 A1 *   5/2006   De Bont .............. A61K 31/502
                                                          514/252.02

OTHER PUBLICATIONS

De Medina et al. ("Synthesis of New Alkylaminooxysterols with Potent Cell Differentiating Activities: Identification of Leads for the Treatment of Cancer and Neurodegenerative Diseases" J. Med. Chem. 2009, 52, 7765-7777).*

* cited by examiner

*Primary Examiner* — Yong S. Chong
(74) *Attorney, Agent, or Firm* — Whitham & Cook, P.C.

(57) ABSTRACT

Dendrogenin A and antineoplastic agents for the treatment of chemosensitive or chemoresistant tumors. The invention concerns a kit-of-parts comprising 5α-hydroxy-6β-[2-(1H-imidazol-4-yl)ethylamino]cholestan-3β-ol (Dendrogenin A) or a pharmaceutically acceptable salt thereof and an antineoplastic agent for use in the treatment of cancer. Furthermore, the invention concerns Dendrogenin A or a pharmaceutically acceptable salt thereof for use for treating a chemoresistant cancer.

18 Claims, 26 Drawing Sheets

DDA/DNR 25:1

DDA/DNR 25:1

DDA/AraC 5:1

DDA/AraC 5:1

DDA/DNR 25:1

DDA/DNR 25:1

DDA/DNR
25:1

DDA/DNR
25:1

DDA/AraC
5:1

DDA/AraC
5:1

DDA/AraC
5:1

DDA/AraC
5:1

DDA/5FU ratio 1:154

DDA/5FU ratio 1:154

DDA/5FU ratio 1:154

DDA/5FU ratio 1:154

DDA/5FU ratio 1:154

DDA/5FU ratio 1:154

DDA/5FU ratio 1:154

DDA/5FU ratio 1:154

DDA/CisP ratio 1:1.33

DDA/CisP ratio 1:1.33

DDA/CisP ratio 1:1.33

DDA/CisP ratio 1:1.33

DDA/CisP ratio 1:1.33

DDA/CisP ratio 1:1.33

DDA/CisP ratio 1:1.33

DDA/CisP ratio 1:1.33

DDA/CisP ratio 1:1.33

DDA/Bortezomib ratio 100:1

DDA/Bortezomib ratio 100:1

DDA/Bortezomib ratio 100:1

DDA/Bortezomib ratio 100:1

DDA/arsenic trioxide 1:1

DDA/arsenic trioxide 1:1

DDA/arsenic trioxide 1:1

DDA/arsenic trioxide 1:1

DDA/ATRA 1:2

DDA/ATRA 1:2

DDA/ATRA 1:2

DDA/ATRA 1:2

DENDROGENIN A AND ANTINEOPLASTIC AGENTS FOR THE TREATMENT OF CHEMOSENSITIVE OR CHEMORESISTANT TUMORS

The present application is filed pursuant to 35 U.S.C. 371 as a U.S. National Phase application of International Patent Application No. PCT/EP2014/068772, which was filed Sep. 3, 2014, claiming the benefit of priority to European Patent Application No. 13306206.7, which was filed on Sep. 4, 2013. The entire text of the aforementioned applications is incorporated herein by reference in its entirety.

FIELD OF THE INVENTION

The present invention concerns the treatment of cancer.

More specifically, the present invention concerns a kit-of-parts comprising 5α-hydroxy-6β-[2-(1H-imidazol-4-yl)ethylamino]cholestan-3β-ol or a pharmaceutically acceptable salt thereof and an antineoplastic agent for use in the treatment of cancer.

Furthermore, the present invention concerns 5α-hydroxy-6β-[2-(1H-imidazol-4-yl)ethylamino]cholestan-3β-ol or a pharmaceutically acceptable salt thereof for use for treatment of a chemoresistant cancer.

BACKGROUND

Cancer management involves surgery, radiotherapy and chemotherapy, which may be used alone or in combination, either simultaneously or sequentially.

Chemotherapy employs antineoplastic agents which are drugs that prevent or inhibit the maturation and proliferation of neoplasms. Antineoplastic agents work by effectively targeting fast-dividing cells. As antineoplastic agents affect cell division, tumors with high growth fractions (such as acute myelogenous leukemia and the aggressive lymphomas, including Hodgkin's disease) are more sensitive to chemotherapy, as a larger proportion of the targeted cells are undergoing cell division at any time. Malignancies with slower growth rates, such as indolent lymphomas, tend to respond to chemotherapy much more modestly.

However, the development of chemoresistance is a persistent problem during chemotherapy treatment. For instance, the conventional treatment of acute myeloid leukemia (AML) comprises the combined administration of cytarabine with an anthracycline, such as daunorubicin. 5-year overall survival rate is 40% in young adults and around 10% for elderly patients. Response rates dramatically vary with ageing, from 40% to 55% in patients older than 60 years and from 24% to 33% in patients older than 70 years. This is even worse for elderly with adverse cytogenetic profiles and death within 30 days following therapy ranges from 10% to 50% with increasing age and worsening. Furthermore, the restriction of the use of these molecules is due also to secondary effects, and in particular the emergence of chronic cardiac toxicity (linked to anthracyclines). The intensive chemotherapy-related toxic death rate is 10-20% in patients over 60 years.

With this risk-benefit profile of the conventional regimen, only 30% of elderly with newly diagnosed AML receive antineoplastic chemotherapy. Over the last decades, there was only modest improvement of outcomes for younger patients with AML, but none for adults older than 60 years (most of patients with AML). This data underline the need of new combination approaches both to reduce dosage regimens of antineoplastic agents to treat chemosensitive tumors and by-pass resistance of chemoresistant tumors to antineoplastic agent.

Two main issues have to be overcome in order to reach these goals: 1) chemoresistance; 2) intrinsic toxicity of antineoplastic drugs.

Various hypotheses have been proposed to account for the phenomenon of chemoresistance. The hypothesis include altered transport of the drug across the plasma membrane, genetic responses, enhanced DNA repair, alteration in target molecules, access to target cells, metabolic effects and growth factors. Recently, small pumps on the surface of cancer cells that actively move chemotherapy drugs from inside the cell to the outside have been identified. Research on p-glycoprotein and other such chemotherapy efflux pumps is currently ongoing. Medications inhibiting the function of p-glycoprotein have been explored to enhance the efficacy of chemotherapy. However, this approach failed during clinical evaluation. (Kolitz J E et al, Blood 2010; Burnett A K et al, Br J Hematol 2009).

There is an urgent need to develop new therapy regimens to overcome chemoresistance of tumors or to increase the sensibility of tumors to antineoplastic drugs.

The pharmaceutically active compound 5α-hydroxy-6β-[2-(1H-imidazol-4-yl)ethylamino]cholestan-3β-ol is known under the name Dendrogenin A. Its structural formula I is the following one:

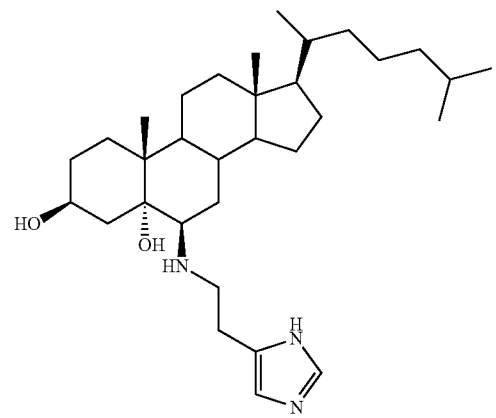

Formula I

Dendrogenin A is disclosed in WO03/89449 and de Medina et al (*J. Med. Chem.*, 2009 and *Nature Commun.* 2013) and has been shown to induce cell death of various tumor cell lines.

Dendrogenin A is the first endogenous steroidal alkaloid identified in mammals. It was established that Dendrogenin A is enzymatically formed in mammalian tissue extracts and is a selective inhibitor of cholesterol epoxide hydrolase (de Medina et al., *Nature Communications*, 2013). Dendrogenin A induces tumor cell differentiation and immune cell infiltration. The properties of Dendrogenin A and its decreased level in tumors suggest a physiological function in maintaining cell integrity and differentiation.

Surprisingly, the present inventors have found that Dendrogenin A is able to restore the sensibility of tumors which are chemoresistant to an antineoplastic agent or to increase the effects of antineoplastic agents to tumors, which allows in turn reducing the effective cytotoxic dose of antineoplastic agents against chemosensitive tumors.

SUMMARY

The object of the present invention is a kit-of-parts comprising 5α-hydroxy-6β-[2-(1H-imidazol-4-yl)ethylamino]cholestan-3β-ol or a pharmaceutically acceptable salt thereof and an antineoplastic agent for use in the treatment of cancer.

In one embodiment, the cancer is acinar adenocarcinoma, acinar carcinoma, acral-lentiginous melanoma, actinic keratosis, adenocarcinoma, adenocystic carcinoma, adenosquamous carcinoma, adnexal carcinoma, adrenal rest tumor, adrenocortical carcinoma, aldosterone secreting carcinoma, alveolar soft part sarcoma, amelanotic melanoma, ameloblastic thyroid carcinoma, angiosarcoma, apocrine carcinoma, Askin's tumor, astrocytoma, basal cell carcinoma, basaloid carcinoma, basosquamous cell carcinoma, biliary cancer, bone cancer, bone marrow cancer, botryoid sarcoma, brain cancer, breast cancer, bronchioalveolar carcinoma, bronchogenic adenocarcinoma, bronchogenic carcinoma, carcinoma ex pleomorphic adenoma, cervical cancer, chloroma, cholangiocellular carcinoma, chondrosarcoma, choriocarcinoma, choroid plexus carcinoma, clear cell adenocarcinoma, colon cancer, colorectal cancer, comedocarcinoma, cortisol-producing carcinoma, cylindrical cell carcinoma, dedifferentiated liposarcoma, ductal adenocarcinoma of the prostate, ductal carcinoma, ductal carcinoma in situ, duodenal cancer, eccrine carcinoma, embryonal carcinoma, endometrial carcinoma, endometrial stromal carcinoma, epithelioid sarcoma, esophageal cancer, Ewing's sarcoma, exophytic carcinoma, fibroblastic sarcoma, fibrocarcinoma, fibrolamellar carcinoma, fibrosarcoma, follicular thyroid carcinoma, gallbladder cancer, gastric adenocarcinoma, giant cell carcinoma, giant cell sarcoma, giant cell tumor of bone, glioma, glioblastoma multiforme, granulose cell carcinoma, head & neck cancer, hemangioma, hemangiosarcoma, hepatoblastoma, hepatocellular carcinoma, Hürthle cell carcinoma, ileal cancer, infiltrating lobular carcinoma, inflammatory carcinoma of the breast, intraductal carcinoma, intraepidermal carcinoma, jejuna cancer, Kaposi's sarcoma, Krukenberg's tumor, Kulchitsky cell carcinoma, Kupffer cell sarcoma, large cell carcinoma, larynx cancer, lentigo maligna melanoma, liposarcoma, liver cancer, lobular carcinoma, lobular carcinoma in situ, lung cancer, lymphoepithelioma, lymphoepithelioma, lymphosarcoma, malignant melanoma, medullary carcinoma, medullary thyroid carcinoma, medulloblastoma, meningeal carcinoma, Merkel cell carcinoma, micropapillary carcinoma, mixed cell sarcoma, mucinous carcinoma, mucoepidermoid carcinoma, mucosal melanoma, myxoid liposarcoma, myxosarcoma, nasopharyngeal carcinoma, nephroblastoma, neuroblastoma, nodular melanoma, non-clear cell renal cancer, non-small cell lung cancer, oat cell carcinoma, ocular melanoma, oral cancer, osteoid carcinoma, osteosarcoma, ovarian cancer, Paget's carcinoma, pancreatic cancer, pancreatoblastoma, papillary adenocarcinoma, papillary carcinoma, papillary thyroid carcinoma, pelvic cancer, periampullary carcinoma, phyllodes tumor, pituitary cancer, pleomorphic liposarcoma, pleuropulmonary blastoma, primary intraosseous carcinoma, prostate cancer, rectal cancer, renal cell carcinoma, retinoblastoma, rhabdomyosarcoma, round cell liposarcoma, scar cancer, schistosomal bladder cancer, schneiderian carcinoma, sebaceous carcinoma, signet-ring cell carcinoma, skin cancer, small cell lung cancer, small cell osteosarcoma, soft tissue sarcoma, splindle cell carcinoma, spindle cell sarcoma, squamous cell carcinoma, stomach cancer, superficial spreading melanoma, synovial sarcoma, telangiectatic sarcoma, terminal duct carcinoma, testicular cancer, thyroid cancer, transitional cell carcinoma, tubular carcinoma, tumorigenic melanoma, undifferentiated carcinoma, urachal adenocarcinoma, urinary bladder cancer, uterine cancer, uterine corpus carcinoma, uveal melanoma, aginal cancer, cerrucous carcinoma, villous carcinoma, well-differentiated liposarcoma, Wilm's tubor or yolk sac tumor.

In one embodiment, the kit-of-parts of the invention is for use in the treatment of cancer in a patient with a tumor that is chemoresistant to said antineoplastic agent when not administered in combination with 5α-hydroxy-6β-[2-(1H-imidazol-4-yl)ethylamino]cholestan-3β-ol or a pharmaceutically acceptable salt thereof to said patient.

In another embodiment, the kit-of-parts of the invention is for use in the treatment of cancer in a patient with a tumor that is chemosensitive to said antineoplastic agent, and the dose of antineoplastic agent administered to said patient in combination with 5α-hydroxy-6β-[2-(1H-imidazol-4-yl)ethylamino]cholestan-3β-ol or a pharmaceutically acceptable salt thereof is lower than the dose of antineoplastic agent administered when not administered in combination with 5α-hydroxy-6β-[2-(1H-imidazol-4-yl)ethylamino]cholestan-3β-ol or a pharmaceutically acceptable salt thereof to said patient.

In one more particular embodiment, the cancer is a hematological cancer or blood cancer, such as leukemia, in particular acute myeloid leukemia or acute lymphocytic leukemia, lymphoma, in particular non-Hodgkin lymphoma or multiple myeloma.

In one embodiment, the antineoplastic agent is a DNA-damaging agent such as camptothecin, irinotecan, topotecan, amsacrine, etoposide, etoposide phosphate, teniposide, cisplatin, carboplatin, oxaliplatin, cyclophosphamide, chlorambucil, chlormethine, busulfan, treosulfan or thiotepa, an antitumor antibiotic such as daunorubicin, doxorubicin, epirubicin, idarubicin, mitoxantrone, valrubicin, actinomycin D, mitomycin, bleomycin or plicamycin, an anti-metabolite such as 5-fluorouracil, cytarabine, fludarabine or methotrexate, an antimitotic such as paclitaxel, docetaxel, vinblastine, vincristine, vindesine or vinorelbine, or miscellaneous antineoplastic agents such as Bortezomib, all-trans retinoic acid or arsenic trioxide, or a combined product thereof.

In one embodiment, the antineoplastic agent is daunorubicin combined with cytarabine.

In one embodiment, the antineoplastic agent is fluorouracil combined with cisplatin.

In one embodiment, the antineoplastic agent is arsenic trioxide combined with all-trans retinoic acid.

In one embodiment, 5α-hydroxy-6β-[2-(1H-imidazol-4-yl)ethylamino]cholestan-3β-ol or a pharmaceutically acceptable salt thereof and the antineoplastic agent are simultaneously administered.

In one embodiment, 5α-hydroxy-6β-[2-(1H-imidazol-4-yl)ethylamino]cholestan-3β-ol or a pharmaceutically acceptable salt thereof and the antineoplastic agent are sequentially administered.

Another object of the present invention is 5α-hydroxy-6β-[2-(1H-imidazol-4-yl)ethylamino]cholestan-3β-ol or a pharmaceutically acceptable salt thereof for use for treating a chemoresistant cancer.

In one embodiment, said cancer is chemoresistant to daunorubicin, cytarabine, fluorouracil, cisplatin, all-trans retinoic acid, arsenic trioxide, Bortezomib, or a combination thereof.

BRIEF DESCRIPTION OF THE FIGURES

In the figures, the following abbreviations are used:
MTT=Methylthiazolyldiphenyl-tetrazolium bromide Conc.=concentration
DNR or Dauno=Daunorubicin
Arac=Cytarabine
5-FU=5-Fluorouracil
CisP=Cisplatin
DDA=Dendrogenin A
bort.=Bortezomib
ATO=arsenic trioxide
ATRA=all-trans retinoic acid

FIG. 6A is a bar diagram showing cell death induction of the combination Dendrogenin A and Cytarabine in the chemoresistant cancer cell line KG1a.

FIG. 6B is a bar diagram showing cell death induction of the combination Dendrogenin A and Daunorubicin in the chemoresistant cancer cell line KG1a.

FIG. 7B is a bar diagram showing cell death induction of the combination Dendrogenin A and Daunorubicin drug sensitive cancer cell line KG1.

FIG. 8A is a curve diagram showing the effect of the combination of Dendrogenin A and Daunorubicin (25:1 molecular ratio) on cell viability of the chemoresistant cancer cell line KG1a.

FIG. 8B is an isobologram representation showing the synergistic effect of the combination of Dendrogenin A and Daunorubicin on cell viability of the chemoresistant cancer cell line KG1a.

FIG. 8C is a curve diagram showing the combination index (CI) values on cell viability in the chemoresistant cancer cell line KG1a for the Dendrogenin A and Daunorubicin association.

FIG. 9A is a curve diagram showing the effect of the combination of Dendrogenin A and Cytarabine on cell viability in the chemoresistant cancer cell line KG1a.

FIG. 9B is an isobologram representation showing the synergistic effect of the combination of Dendrogenin A and Cytarabine (5:1 molecular ratio) on cell viability of the chemoresistant cancer cell line KG1a.

FIG. 9C is a curve diagram showing the combination index (CI) values on cell viability of the chemoresistant cancer cell line KG1a for the combination of Dendrogenin A and Cytarabine.

FIG. 16A is a curve diagram showing the effect of combination of Dendrogenin A and 5-fluorouracil (1:154 molecular ratio) on cell viability of the chemoresistant cancer cell line KG1a.

FIG. 16B is an isobologram representation showing the synergistic effect of the combination of Dendrogenin A and 5-Fluorouracil on cell viability of chemoresistant cancer cell line KG1a.

FIG. 16C is a curve diagram showing the combination index (CI) values on cell viability in the chemoresistant cancer cell line KG1a for the combination of Dendrogenin A and 5-Fluorouracil.

FIG. 19A is a curve diagram showing the effect of the combination of Dendrogenin A and Cisplatin (1:1.33 molecular ratio) on cell viability of the chemoresistant cancer cell line KG1a.

FIG. 19B is an isobologram representation showing the synergistic effect of the combination of Dendrogenin A and Cisplatin on cell viability of chemoresistant cancer cell line KG1a.

FIG. 19C is a curve diagram showing the combination index (CI) values on cell viability in the chemoresistant cancer cell line KG1a for the combination of Dendrogenin A and Cisplatin.

DETAILED DESCRIPTION

Figure 1:
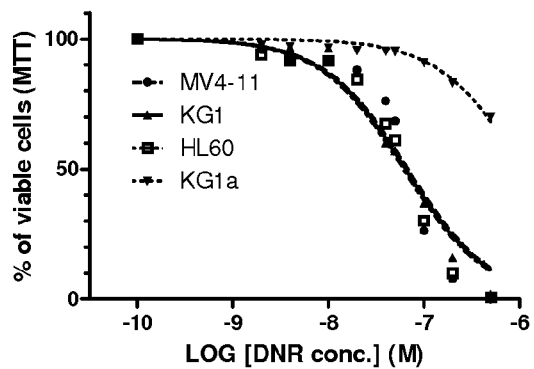
FIG. 1 is a curve diagram showing the effect of Daunorubicin on cell viability of the cancer cell lines MV4-11, KG1, KG1a and HL60.

One object of the present invention is a kit-of-parts comprising 5α-hydroxy-6β-[2-(1H-imidazol-4-yl)ethyl-amino]cholestan-3β-ol (Dendrogenin A) or a pharmaceutically acceptable salt thereof and an antineoplastic agent for use in the treatment of cancer.

By "kit-of-parts", it is meant a combined preparation wherein the active ingredients are physically separated for use in a combined therapy by simultaneous administration or sequential administration to the patient.

Hence, according to the present invention, Dendrogenin A or a pharmaceutically acceptable salt thereof and the antineoplastic agent are administered to the patient in a separate form, either simultaneously or sequentially, for the treatment of cancer.

As used herein, the term "cancer" refers to the physiological condition in subjects that is characterized by unregulated or dysregulated cell growth or death. The term "cancer" includes solid tumors and blood born tumors, whether malignant or benign.

The present invention relates to the treatment of chemoresistant cancers, as well as the treatment of chemosensitive cancers.

By "chemoresistant cancer", it is meant a cancer in a patient where the proliferation of cancer cells cannot be prevented or inhibited by means of an antineoplastic agent or a combination of antineoplastic agents usually used to treat such cancer, at an acceptable dose to the patient. Tumors can be intrinsically resistant prior to chemotherapy, or resistance may be acquired during treatment by tumors that are initially sensitive to chemotherapy.

By "chemosensitive cancer", it is meant a cancer in a patient which is responsive to the effects of an antineoplastic agent, i.e. where the proliferation of cancer cells can be prevented by means of said antineoplastic agent at an acceptable dose to the patient.

By "acceptable dose to the patient", it is meant a dose which does not cause treatment arrest due to side effects.

Examples of cancer include, but are not limited to:

Acinar adenocarcinoma, acinar carcinoma, acral-lentiginous melanoma, actinic keratosis, adenocarcinoma, adenocystic carcinoma, adenosquamous carcinoma, adnexal carcinoma, adrenal rest tumor, adrenocortical carcinoma, aldosterone secreting carcinoma, alveolar soft part sarcoma, amelanotic melanoma, ameloblastic thyroid carcinoma, angiosarcoma, apocrine carcinoma, Askin's tumor, astrocytoma, basal cell carcinoma, basaloid carcinoma, basosquamous cell carcinoma, biliary cancer, bone cancer, bone marrow cancer, botryoid sarcoma, brain cancer, breast cancer, bronchioalveolar carcinoma, bronchogenic adenocarcinoma, bronchogenic carcinoma, carcinoma ex pleomorphic adenoma, cervical cancer, chloroma, cholangiocellular carcinoma, chondrosarcoma, choriocarcinoma, choroid plexus carcinoma, clear cell adenocarcinoma, colon cancer, colorectal cancer, comedocarcinoma, cortisol-producing carcinoma, cylindrical cell carcinoma, dedifferentiated liposarcoma, ductal adenocarcinoma of the prostate, ductal carcinoma, ductal carcinoma in situ, duodenal cancer, eccrine carcinoma, embryonal carcinoma, endometrial carcinoma, endometrial stromal carcinoma, epithelioid sarcoma, esophageal cancer, Ewing's sarcoma, exophytic carcinoma, fibroblastic sarcoma, fibrocarcinoma, fibrolamellar carcinoma, fibrosarcoma, follicular thyroid carcinoma, gallbladder cancer, gastric adenocarcinoma, giant cell carcinoma, giant cell sarcoma, giant cell tumor of bone, glioma, glioblastoma multiforme, granulose cell carcinoma, head & neck cancer, hemangioma, hemangiosarcoma, hepatoblastoma, hepatocellular carcinoma, Hürthle cell carcinoma, ileal cancer, infiltrating lobular carcinoma, inflammatory carcinoma of the breast, intraductal carcinoma, intraepidermal carcinoma, jejuna cancer, Kaposi's sarcoma, Krukenberg's tumor, Kulchitsky cell carcinoma, Kupffer cell sarcoma, large cell carcinoma, larynx cancer, lentigo maligna melanoma, liposarcoma, liver cancer, lobular carcinoma, lobular carcinoma in situ, lung cancer, lymphoepithelioma, lymphoepithelioma, lymphosarcoma, malignant melanoma, medullary carcinoma, medullary thyroid carcinoma, medulloblastoma, meningeal carcinoma, Merkel cell carcinoma, micropapillary carcinoma, mixed cell sarcoma, mucinous carcinoma, mucoepidermoid carcinoma, mucosal melanoma, myxoid liposarcoma, myxosarcoma, nasopharyngeal carcinoma, nephroblastoma, neuroblastoma, nodular melanoma, non-clear cell renal cancer, non-small cell lung cancer, oat cell carcinoma, ocular melanoma, oral cancer, osteoid carcinoma, osteosarcoma, ovarian cancer, Paget's carcinoma, pancreatic cancer, pancreatoblastoma, papillary adenocarcinoma, papillary carcinoma, papillary thyroid carcinoma, pelvic cancer, periampullary carcinoma, phyllodes tumor, pituitary cancer, pleomorphic liposarcoma, pleuropulmonary blastoma, primary intraosseous carcinoma, prostate cancer, rectal cancer, renal cell carcinoma, retinoblastoma, rhabdomyosarcoma, round cell liposarcoma, scar cancer, schistosomal bladder cancer, schneiderian carcinoma, sebaceous carcinoma, signet-ring cell carcinoma, skin cancer, small cell lung cancer, small cell osteosarcoma, soft tissue sarcoma, splindle cell carcinoma, spindle cell sarcoma, squamous cell carcinoma, stomach cancer, superficial spreading melanoma, synovial sarcoma, telangiectatic sarcoma, terminal duct carcinoma, testicular cancer, thyroid cancer, transitional cell carcinoma, tubular carcinoma, tumorigenic melanoma, undifferentiated carcinoma, urachal adenocarcinoma, urinary bladder cancer, uterine cancer, uterine corpus carcinoma, uveal melanoma, aginal cancer, cerrucous carcinoma, villous carcinoma, well-differentiated liposarcoma, Wilm's tubor or yolk sac tumor.

In one embodiment, the cancer is melanoma, carcinoma, lymphoma, blastoma, sarcoma, liposarcoma, myeloma and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, aggressive or metastatic melanoma as well as head and neck cancer.

The present invention pertains more particularly to hematological or blood cancer, such as leukemia, in particular acute myeloid leukemia or acute lymphocytic leukemia, lymphoma, in particular non-Hodgkin lymphoma or multiple myeloma.

As used herein, the term "antineoplastic agent" refers to a drug or a combination of drugs that prevents or inhibits the maturation and proliferation of tumors.

Antineoplastic agents are classified according to their mode of action. The various classes of antineoplastic agents include in particular DNA-damaging agents, anti-tumor antibiotics, antimetabolites, antimitotics and miscellaneous antineoplastic agents.

DNA-damaging agents include alkylating agents and topoisomerase inhibitors.

Topoisomerase inhibitors (Anatomical Therapeutic Chemical Classification (ATC) code L01CB and L01XX) are agents that block type I or type II topoisomerases interfering thus with both transcription and replication of DNA by upsetting proper DNA supercoiling. Examples of type I topoisomerase inhibitors include camptothecins, irinotecan and topotecan. Examples of type II inhibitors include amsacrine, etoposide, etoposide phosphate, and teniposide.

Alkylating agents (ATC code L01A) are so named because of their ability to alkylate many nucleophilic functional groups under conditions present in cells. They impair cell function by forming covalent bonds with the amino, carboxyl, sulfhydryl, and phosphate groups in biologically important molecules. Examples of alkylating agents include cyclophosphamide, chlorambucil, chlormethine, busulfan, treosulfan, thiotepa and platinum compounds, such as cisplatin, carbolatin, oxaliplatin.

Anti-tumor antibiotics include mainly anthracyclines (ATC code: L01DB), such as daunorubicin, doxorubicin, epirubicin, idarubicin, mitoxantrone, or valrubicin, and other anti-tumor antibiotics (ATC code: L01DC) such as actinomycin D, mitomycin, bleomycin or plicamycin.

Anti-metabolites (ATC code L01B) are similar in structure to naturally occurring compounds that are required for the viability and division of a cell. The efficacy of the most important anti-metabolites against a range of tumor cells is based on the inhibition of purine or pyrimidine nucleoside synthesis pathway that are required for DNA synthesis.

Anti-metabolites can be divided into several classes, including folate antagonists such as methotrexate, purine antagonists such as fludarabine and pyrimidine antagonists such as fluorouracil and cytarabine.

Antimitotics include taxanes and vinca alkaloids.

Taxanes (ATC code: L01CD) interfere with microtubules. They block cell growth by stopping mitosis. Examples of taxanes include paclitaxel, and docetaxel.

*Vinca* alkaloids (ATC code: L01CA) bind to specific sites on tubulin, inhibiting the assembly of tubulin into microtubules (M phase of the cell cycle). They are derived from the Madagascar periwinkle, *Catharanthus roseus* (formerly known as *Vinca rosea*).

Examples of vinca alkaloids are vincristine, vinblastine, vinorelbine, vindesine.

Miscellaneous antineoplastic agents include for instance Bortezomib, all-trans retinoic acid and arsenic trioxide.

In one embodiment, the antineoplastic agent is a DNA-damaging agent such as camptothecin, irinotecan, topotecan, amsacrine, etoposide, etoposide phosphate, teniposide, cisplatin, carboplatin, oxaliplatin, cyclophosphamide, chlorambucil, chlormethine, busulfan, treosulfan or thiotepa, an antitumor antibiotic such as daunorubicin, doxorubicin, epirubicin, idarubicin, mitoxantrone, valrubicin, actinomycin D, mitomycin, bleomycin or plicamycin, an anti-metabolite such as 5-fluorouracil, cytarabine, fludarabine or methotrexate, an antimitotic such as paclitaxel, docetaxel, vinblastine, vincristine, vindesine or vinorelbine, or Bortezomib, all-trans retinoic acid, arsenic trioxide or a combined product thereof.

In one embodiment, the antineoplastic agent is a combined product of at least two active ingredients. The two active ingredients can be administered separately to the patient or administered in the same preparation.

In one embodiment, the antineoplastic agent is daunorubicin combined with cytarabine.

In one embodiment, the antineoplastic agent is fluorouracil combined with cisplatin.

In one embodiment, the antineoplastic agent is arsenic trioxide combined with all-trans retinoic acid.

Pharmaceutically acceptable salts of Dendrogenin A include (but are not limited to) acid addition salts formed with an acid, for instance selected from the group consisting of an inorganic acid, an acyclic aliphatic carboxylic or sulfonic acid comprising no more than 8 carbon atoms, and an aromatic carboxylic or sulfonic acid comprising no more than 4 aryl group.

Preferred acids are selected from the group consisting of hydrochloride acid, sulfuric acid, acetic acid, L-lactic acid (2(S)-hydroxypropanoic acid), tartaric acid, L-malic acid, succinic acid, malonic acid, fumaric acid, glutaric acid, L-tartaric acid, D-tartaric acid, 2(S)-hydroxypropanoic acid, citric acid, malonic acid, and tartric acid (D or L), mesylic acid, benzenesulfonic acid, benzoic acid, 4-methylbenzenesulfonic acid, and pamoic acid (4,4'methylenebis(3-hydroxy-2-naphtoic acid)).

The present invention is useful for the treatment of chemoresistant tumors, i.e. tumors for which a treatment with an antineoplastic agent is inefficient. Tumors may be intrinsically chemoresistant or develop resistance to chemotherapy during treatment.

Therefore, in one embodiment, Dendrogenin A or a pharmaceutically acceptable salt thereof is used in combined therapy with an antineoplastic agent to restore the sensibility of a tumor which is resistant to this antineoplastic agent, in particular to restore the cell death induction of this antineoplastic agent.

Thus, in one embodiment, the kit-of-parts of the invention is for use in the treatment of cancer in a patient with a tumor that is chemoresistant to said antineoplastic agent when not administered in combination with 5α-hydroxy-6β-[2-(1H-imidazol-4-yl)ethylamino]cholestan-3β-ol or a pharmaceutically acceptable salt thereof to said patient.

In another embodiment, Dendrogenin A or a pharmaceutically acceptable salt thereof is used in combined therapy with an antineoplastic agent for decreasing the effective dose of this antineoplastic agent. In this embodiment, Dendrogenin A is able to potentiate the therapeutic effect of the antineoplastic agent and therefore may be used to limit the intrinsic toxicity of an antineoplastic agent through the reduction of the effective dose, thereby allowing for example the treatment of an eldery patient who is initially not eligible for treatment with said antineoplastic agent.

Thus, in another embodiment, the kit-of-parts of the invention is for use in the treatment of cancer in a patient with a tumor that is chemosensitive to said antineoplastic agent, and the dose of antineoplastic agent administered to said patient in combination with 5α-hydroxy-6β-[2-(1H-imidazol-4-yl)ethylamino]cholestan-3β-ol or a pharmaceutically acceptable salt thereof is lower than the dose of antineoplastic agent when not administered in combination with 5α-hydroxy-6β-[2-(1H-imidazol-4-yl)ethylamino]cholestan-3β-ol or a pharmaceutically acceptable salt thereof to said patient.

According to the present invention, Dendrogenin A may be administered as a pharmaceutical formulation in a therapeutically effective amount by any of the accepted modes of administration, preferably by intra-venous or oral route.

Suitable dosage ranges are typically from 0.1 to 50 000 µg/kg of body weight daily, preferably from 1 000 to 40 000 µg/kg of body weight daily, and most preferably from 40 000 µg/kg of body weight daily, depending upon numerous factors such as the severity of the cancer to be treated, the age and relative health of the subject, the route and the form of administration.

The antineoplastic agent may be administered as a pharmaceutical formulation in a conventional manner, depending upon the type of cancer to be treated and its severity, the age and relative health of the subject, the potency of the antineoplastic agent used, the route and form of administration, the indication towards which the administration is directed, and the preferences and experience of the medical practitioner involved. One of ordinary skill in the art of treating such diseases will be able in reliance upon personal knowledge, to ascertain a therapeutically effective amount of the antineoplastic agent of the present invention for a given cancer.

The pharmaceutical compositions may comprise of conventional ingredients in conventional proportions, with or without additional active compounds or principles, and the unit dosage forms may contain any suitable effective amount of the active ingredient commensurate with the intended daily dosage range to be employed.

In one embodiment, Dendrogenin A or a pharmaceutically acceptable salt thereof and the antineoplastic agent are simultaneously administered.

In another embodiment, Dendrogenin A or a pharmaceutically acceptable salt thereof and the antineoplastic agent are sequentially administered.

In a particular and preferred embodiment, Dendrogenin A or a pharmaceutically acceptable salt thereof is administered prior to the antineoplastic agent.

In a particular embodiment, Dendrogenin A or a pharmaceutically acceptable salt thereof is administered after the antineoplastic agent.

Another object of the present invention is a method for treating cancer in a patient comprising administering to said patient a therapeutically effective amount of 5α-hydroxy-6β-[2-(1H-imidazol-4-yl)ethylamino]cholestan-3β-ol (Dendrogenin A) or a pharmaceutically acceptable salt thereof and a therapeutically effective amount of an antineoplastic agent, as described above.

Another object of the present invention is Dendrogenin A or a pharmaceutically acceptable salt thereof for use for treating chemoresistant cancer, wherein Dendrogenin A is used as the only active ingredient, i.e. not in combination with any another antineoplastic agent.

In one embodiment, said cancer is chemoresistant to daunorubicin, cytarabine, fluorouracil, cisplatin, all-trans retinoic acid, arsenic trioxide, Bortezomib, or a combination thereof.

In one embodiment, said chemoresistant cancer is a hematological or blood cancer, such as leukemia, in particular acute myeloid leukemia or acute lymphocytic leukemia, lymphoma, in particular non-Hodgkin lymphoma and multiple myeloma.

In one embodiment, said cancer is not metastatic melanoma resistant to dacarbazine.

In one embodiment, said cancer is not B16F10 metastatic melanoma.

B16F10 metastatic melanoma is a murine melanoma which does not bear any mutation in the Braf gene, in the ras genes and in the p53 gene.

In one embodiment, said cancer is a metastatic melanoma resistant to dacarbazine and said cancer bears a mutation in the ras gene.

In one embodiment, said cancer is a metastatic melanoma resistant to dacarbazine and said cancer bears a mutation in the BRaf gene.

In one embodiment, said cancer is a metastatic melanoma resistant to dacarbazine and said cancer bears a mutation in the p53 gene.

In one embodiment, said cancer is a metastatic melanoma resistant to dacarbazine and said cancer bears a mutation in the ras genes, in the BRaf gene and in the p53 gene.

Another object of the present invention is Dendrogenin A or a pharmaceutically acceptable salt thereof for use for treating a human chemoresistant cancer, wherein Dendrogenin A is used as the only active ingredient, i.e. not in combination with any another antineoplastic agent.

In one embodiment, said human cancer is chemoresistant to daunorubicin, cytarabine, fluorouracil, cisplatin, all-trans retinoic acid, arsenic trioxide, Bortezomib, or a combination thereof.

In one embodiment, said human chemoresistant cancer is a hematological or blood cancer, such as leukemia, in particular acute myeloid leukemia or acute lymphocytic leukemia, lymphoma, in particular non-Hodgkin lymphoma and multiple myeloma.

Another object of the present invention is a method for treating a chemoresistant cancer in a patient comprising administering to said patient a therapeutically effective amount of 5α-hydroxy-6β-[2-(1H-imidazol-4-yl)ethyl-amino]cholestan-3β-ol (Dendrogenin A) or a pharmaceutically acceptable salt thereof.

Another object of the present invention is Dendrogenin A or a pharmaceutically acceptable salt thereof for use in the treatment of cancer in a patient treated with an antineoplastic agent wherein said cancer is chemoresistant to said antineoplastic agent.

In one embodiment, said cancer is chemoresistant to daunorubicin, cytarabine, fluorouracil, cisplatin, all-trans retinoic acid, arsenic trioxide, Bortezomib, or a combination thereof.

In one embodiment, said chemoresistant cancer is a hematological or blood cancer, such as leukemia, in particular acute myeloid leukemia or acute lymphocytic leukemia, lymphoma, in particular non-Hodgkin lymphoma and multiple myeloma.

The present invention is particularly directed to the treatment of a patient having cancer and who is developing a resistance to an antineoplastic agent. In that case, Dendrogenin A may be administered in replacement of the antineoplastic agent to which the cancer is resistant or in combination to this antineoplastic agent.

The present invention is also directed to the improvement of the treatment of a patient having cancer who is under chemotherapy with an antineoplastic agent. In that case, Dendrogenin A may be administered in combination with the antineoplastic agent in order to reduce the dose of antineoplastic agent administered to the patient and thus improve the treatment.

The invention will now be further described in the following examples. These examples are offered to illustrate the invention and should in no way be viewed as limiting the invention.

Experiments were designed to fit with methods previously described by Chou and Talalay to quantify the synergy of drug combinations (Chou Cancer Res 2010 and Chou & Talalay, Eur J biochem 1985). Briefly, effect of drugs alone and in combinations were determined for a 3-5 log scale of concentrations of drugs and with a constant ratio between the two drugs used for co-treatment. Cells were seeded in 96-well plates (50 000 cell/well). Cells were treated just after seeding, for 48 hours. Cell viability was determined with MTT assay. Cells were centrifuged 5 minutes at 1200 rpm, medium removed, 100 µl of MTT solution (1 mg/ml in PBS) added, incubated for 2 hours at 37° C., centrifuged, MTT solution removed and DMSO (100 µl) added to dissolve purple formazan formed by living cells. Absorbance of the solution was determined at 540 nm. This general procedure was used in examples 1 to 5 and 8 to 25.

Example 1

Effect of Daunorubicin on Cell Viability of Phenotypically and Genotypically Different Cancer Cell Lines.

HL60, KG1, KG1a and MV4-11 cells were seeded in 96-well plates (50 000 cells/well). Cells were treated just after seeding with increasing doses of daunorubicin, for 48 hours. Cell viability was determined with MTT assay as follows: cells were centrifuged 5 minutes at 1200 rpm, medium removed, 100 µl of MTT solution (1 mg/ml in PBS) added, incubated for 2 hours at 37° C., centrifuged, MTT solution removed and DMSO (100 µl) added to dissolve purple formazan formed by living cells. Absorbance of the solution was determined at 540 nm.

The percentage of viable cells as a function of Daunorubicin concentration is represented in FIG. 1.

FIG. 1 shows that KG1a cells tend to be resistant to Daunorubicin compared to KG1 cells. HL60 and MV4-11 cells tend to be as sensitive as KG1 cells to Daunorubicin.

Example 2

Effect of Cytarabine on Cell Viability of Phenotypically and Genotypically Different Cancer Cell Lines.

HL60, KG1, KG1a and MV4-11 cells were seeded in 96-well plates (50 000 cells/well). Cells were treated just after seeding with increasing doses of cytarabine, for 48 hours. Cell viability was determined with MTT assay as described in example 1.

Figure 2:
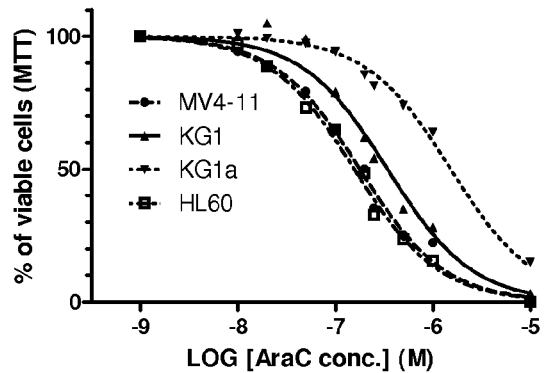
FIG. 2 is a curve diagram showing the effect of Cytarabine on cell viability of the cancer cell lines MV4-11, KG1, KG1a and HL60.

The percentage of viable cells as a function of Cytarabine concentration is represented in FIG. 2.

FIG. 2 shows that KG1a cells tend to be resistant to Cytarabine compared to KG1 cells, but to a lesser extent than Daunorubicin. HL60 and MV4-11 cells tend to be more sensitive than KG1 cells to Cytarabine Example 3

Effect of 5-Fluorouracil on Cell Viability of Phenotypically and Genotypically Different Cancer Cell Lines.

HL60, KG1, KG1a and MV4-11 cells were seeded in 96-well plates (50 000 cells/well). Cells were treated just after seeding with increasing doses of 5-fluorouracil, for 48 hours. Cell viability was determined with MTT assay as described in example 1.

Figure 3:
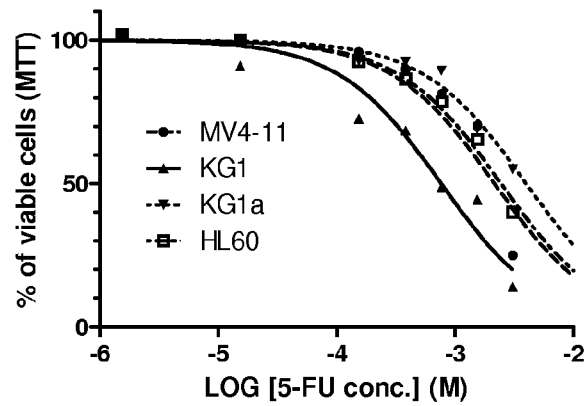
FIG. 3 is a curve diagram showing the effect of 5-fluorouracil on cell viability of the cancer cell lines MV4-11, KG1, KG1a and HL60.

The percentage of viable cells as a function of 5-Fluorouracil concentration is represented in FIG. 3.

FIG. 3 shows that KG1a cells tend to be resistant to 5-Fluororacil compared to KG1 cells, in the same extent than Cytarabine but to a lesser extent than Daunorubicin. HL60 and MV4-11 cells tend to be more resistant to 5-FU compared to Daunorubicin or Cytarabine.

Example 4

Effect of Cisplatin on Cell Viability of Phenotypically and Genotypically Different Cancer Cell Lines.

HL60, KG1, KG1a and MV4-11 cells were seeded in 96-well plates (50 000 cells/well). Cells were treated just after seeding with increasing doses of cisplatin, for 48 hours. Cell viability was determined with MTT assay as described in example 1.

Figure 4:
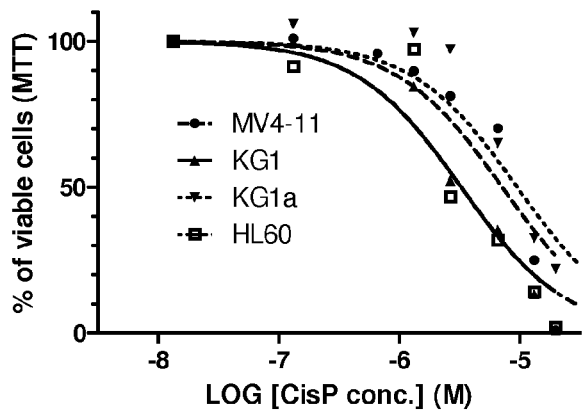
FIG. 4 is a curve diagram showing the effect of Cisplatin on cell viability of the cancer cell lines MV4-11, KG1, KG1a and HL60.

The percentage of viable cells as a function of Cisplatin concentration is represented in FIG. 4.

FIG. 4 shows that KG1a cells tend to be resistant to Cisplatin compared to KG1 cells, but to a lesser extent than Daunorubicin or Cytarabin. HL60 cells are as sensible to Cisplatin as to Daunorubicin and Cytarabine, but MV4-11 cells tend to be more resistant to Cisplatin compared to Daunorubicin or Cytarabine.

Example 5

Effect of Dendrogenin A on Cell Viability of Phenotypically and Genotypically Different Cancer Cell Lines.

HL60, KG1, KG1a and MV4-11 cells were seeded in 96-well plates (50 000 cells/well). Cells were treated just after seeding with increasing doses of Dendrogenin A, for 48 hours. Cell viability was determined with MTT assay as described in example 1.

Figure 5:
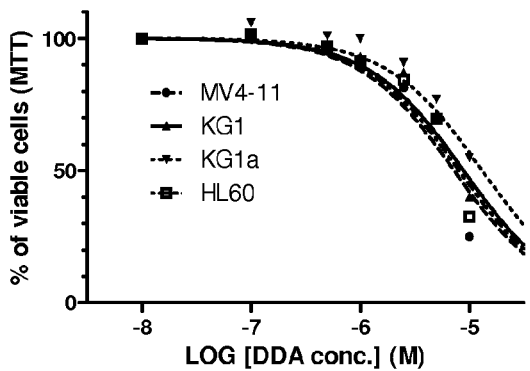
FIG. 5 is a curve diagram showing the effect of Dendrogenin A on cell viability of the cancer cell lines MV4-11, KG1, KG1a and HL60.

The percentage of viable cells as a function of Dendrogenin A concentration is represented in FIG. 5.

FIG. 5 shows that KG1a cells tend to be as sensitive as KG1 cells to Dendrogenin A, while KG1a cells tend to be resistant to Daunorubicin, Cytarabine, 5-Fluororacil and Cisplatin. Moreover, MV4-11 and HL60 cells tend to be as sensitive as KG1 or KG1a cells to Dendrogenin A. These results are indicative on the ability of Dendrogenin A to treat chemoresistant cancers.

Table 1 provides the $IC_{50}$ values determined by using the cell viability assays as described in examples 1 to 5 of the different antineoplastic agents tested in these examples.

TABLE 1

| | | IC 50(μM) | | | | |
|---|---|---|---|---|---|---|
| | | Dendrogenin A | Cytarabin | Daunorubicine | 5-Fluororacil | Cisplatin |
| Cell line | MV4-11 | 7.27 | 0.18 | 0.067 | 2156 | 7.20 |
| | KG1 | 8.86 | 0.34 | 0.064 | 756 | 3.29 |
| | KG1a | 13.2 | 1.53 | 1.08 | 3992 | 9.59 |
| | HL60 | 8.06 | 0.16 | 0.062 | 2448 | 3.29 |

The data of table 1 shows that Dendrogenin A is the drug that presents the smaller $IC_{50}$ difference between chemosensible and chemoresistant cell lines. KG1a/KG1 $IC_{50}$ ratio is 1.5 compared to 2.9 for cisplatin, to 4.5 for cytarabine, 5.3 for 5-fluorouracile and 17 for daunorubicin. This underlies that Dendrogenin A is able to treat tumors efficiently, irrespective to their status of resistance to other antineoplastic agents. Therefore, Dendrogenin A may be a good candidate for treating tumors which are resistant to other antineoplastic agents.

Example 6

Dendrogenin a Restores Cell Death Induction by Daunorubicin and Cytarabine on the Chemoresistant Cancer Cell Line KG1a.

In a 6-microwell plate was seeded $0.5 \cdot 10^6$ cells of KG1a cell line. The same day, Solvant vehicule or different concentrations of Dendrogenin A (final concentrations: 5 and 10 μM) alone or in combination with Daunorubicin (final concentration: 0.5 μM) or cytarabine (final concentration: 1 μM) were added into the well. After 48 hours of incubation, the cells suspensions were centrifuged and cell pellets were resuspended in the Trypan blue solution (0.25% (w/v) in PBS) and counted in a Malassez cell under a light microscope. The results are shown in Figures VIa and VIb (Daunorubicin and Cytarabine respectively).

Figure 6:
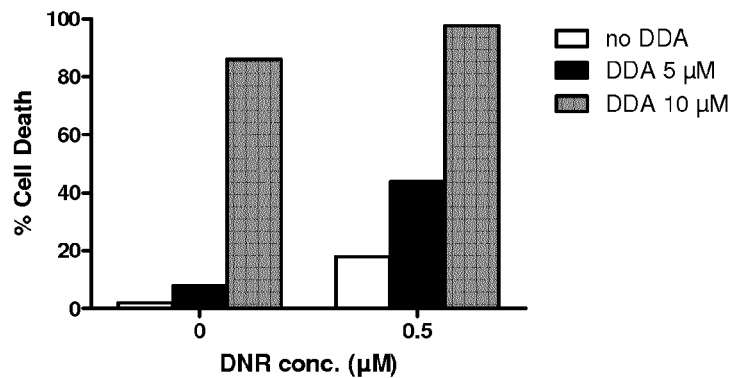
Figure 6:
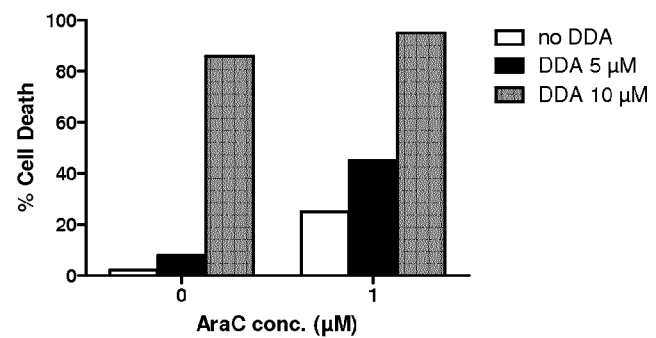

FIG. 6A shows that KG1a cells tend to be resistant to Daunorubicin and that Dendrogenin A is able to abolish this resistance.

FIG. 6B shows that KG1a cells tend to be resistant to Cytarabine and that Dendrogenin A is able to abolish this resistance.

Example 7

Dendrogenin a Increases the Cytotoxic Activity of Daunorubicin and Cytarabine on the Drug Sensitive Cancer Cell Line KG1.

In a 6-microwell plate was seeded $0.5 \cdot 10^6$ cells of KG1 cell line. The same day, Solvant vehicule or Dendrogenin A (final concentrations: 2.5 μM) were added into the well for 24 hours. Then, Daunorubicin (final concentration: 0.05, 0.1, 0.25 and 0.5 μM) or cytarabine (final concentration: 0.1, 0.2, 0.5 and 1 μM) were added to KG1a cells. After the cells were cultured for additional 48 hours, culture suspensions were centrifuged and cell pellets were resuspended in the Trypan blue solution (0.25% (w/v) in PBS) and counted in a Malassez cell under a light microscope. The results are shown in FIGS. 7A and 7B (Daunorubicin and Cytarabine respectively).

Figure 7:
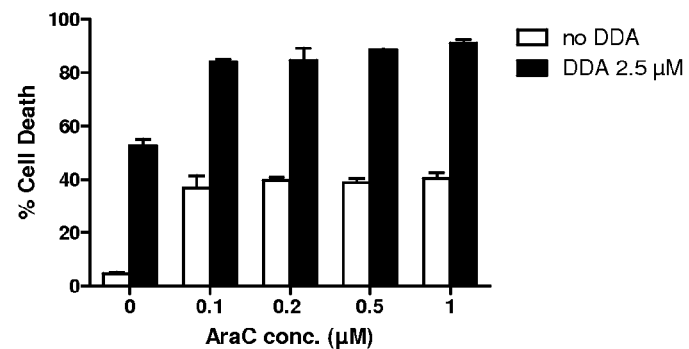
FIG. 7B is a bar diagram showing cell death induction of the combination Dendrogenin A and Cytarabine drug sensitive cancer cell line KG1.
Figure 7:
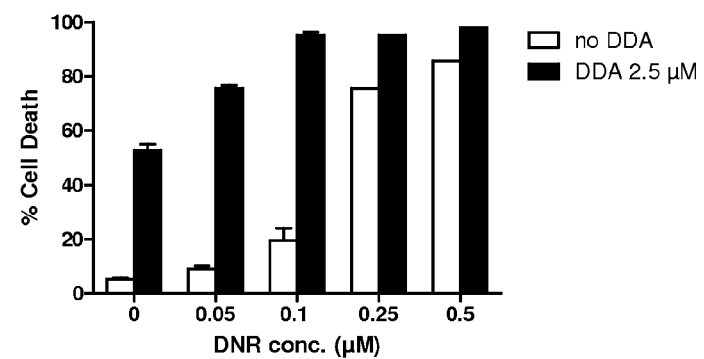

FIG. 7A shows that KG1 cells tend to be sensitive to Daunorubicin compared to KG1a cells and that Dendrogenin A is able to increase this sensibility.

FIG. 7B shows that KG1 cells tend to be sensitive to Cytarabine compared to KG1a cells and that Dendrogenin A is able to increase this sensibility.

Example 8

Synergistic Activity of the Association Dendrogenin A/Daunorubicin on the Chemoresistant Cell Line KG1a KG1a cells were seeded in 96-well plates (50 000 cells/well). Cells were treated just after seeding with increasing doses of Dendrogenin A and Daunorubicin, for 48 hours. Cell viability was determined with MTT assay as described in example 1.

Figure 8:
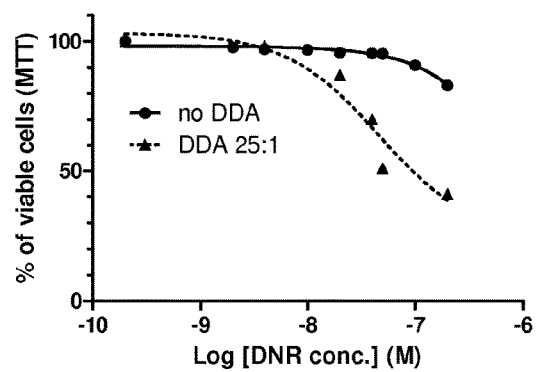
Figure 8:
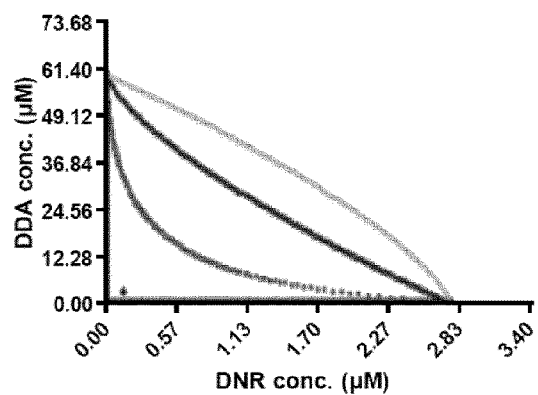
Figure 8:
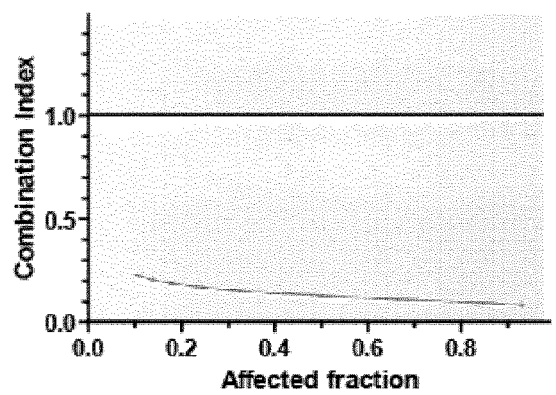

Association of Dendrogenin A and Daunorubicin synergistically reduces viability of the chemoresistant cell line KG1a, as shown in FIGS. 8a, 8b and 8c.

Example 9

Synergistic Activity of the Association Dendrogenin A/Cytarabine on the Chemoresistant Cell Line KG1a KG1a cells were seeded in 96-well plates (50 000 cells/well). Cells were treated just after seeding with increasing doses of Dendrogenin A and Cytarabine, for 48 hours. Cell viability was determined with MTT assay as described in example 1.

Figure 9:
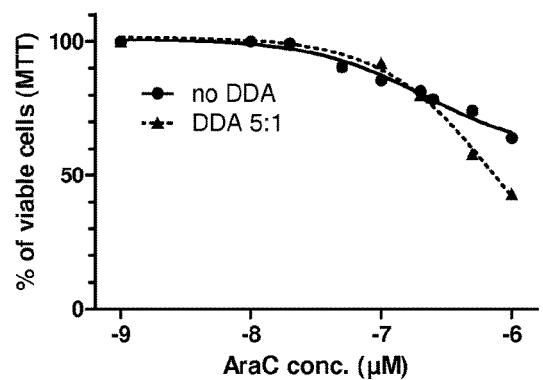
Figure 9:
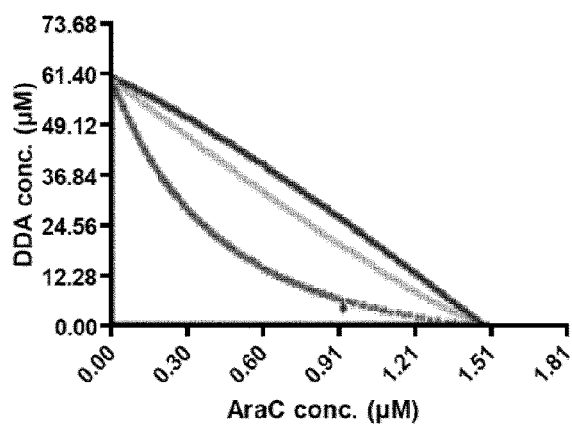
Figure 9:
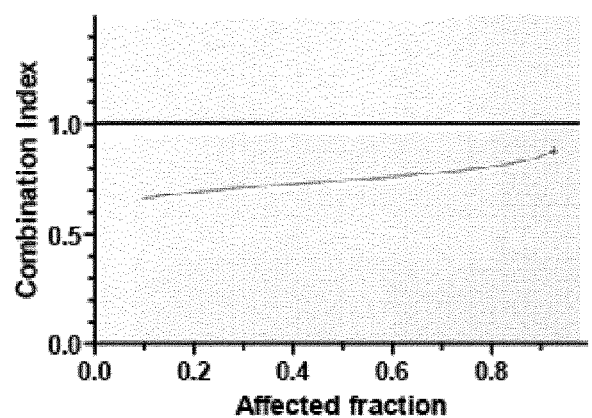

Association of Dendrogenin A and cytarabine synergistically reduces viability of the chemoresistant cell line KG1a, as shown in FIGS. 9a, 9b and 9c.

Example 10

Synergistic Activity of the Association Dendrogenin A/Daunorubicin on the Cytotoxic Drug-Sensitive Cell Line KG1

KG1 cells were seeded in 96-well plates (50 000 cells/well). Cells were treated just after seeding with increasing doses of Dendrogenin A and Daunorubicin, for 48 hours. Cell viability was determined with MTT assay as described in example 1.

Figure 10:
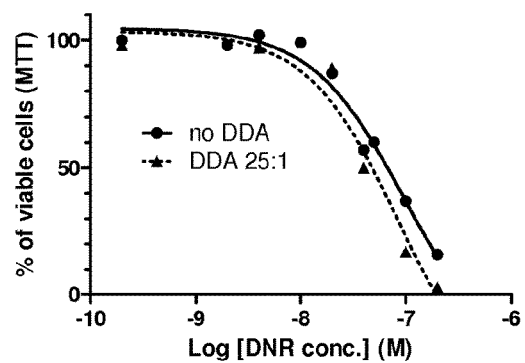
FIG. 10A is a curve diagram showing the effect of the combination of Dendrogenin A and Daunorubicin (25:1 molecular ratio) on cell viability of the drug sensitive cancer cell line KG1.
FIG. 10B is an isobologram representation showing the synergistic effect of the combination of Dendrogenin A and Daunorubicin on cell viability of the drug sensitive cancer cell line KG1.
FIG. 10C is a curve diagram showing the combination index (CI) values on cell viability in the drug sensitive cancer cell line KG1 for the combination of Dendrogenin A and Daunorubicin.
Figure 10:
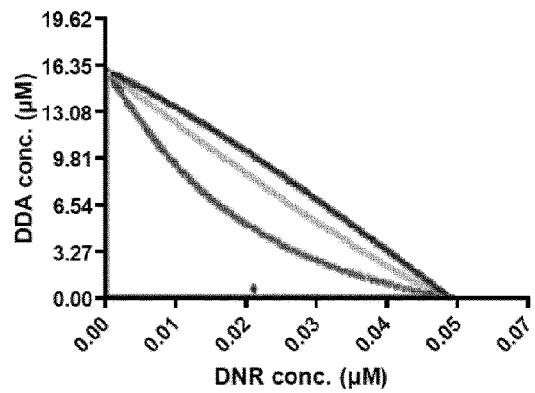
Figure 10:
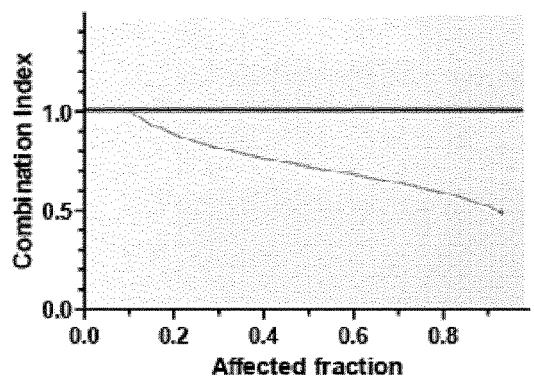

Association of Dendrogenin A and daunorubicin synergistically reduces viability of the drug-sensitive cell line KG1, as shown in FIGS. 10a, 10b and 10c.

Example 11

Synergistic Activity of the Association Dendrogenin A/Daunorubicin on the Cytotoxic Drug-Sensitive Cell Line MV4-11

MV4-11 cells were seeded in 96-well plates (50 000 cells/well). Cells were treated just after seeding with increasing doses of Dendrogenin A and Daunorubicin, for 48 hours. Cell viability was determined with MTT assay as described in example 1.

Figure 11:
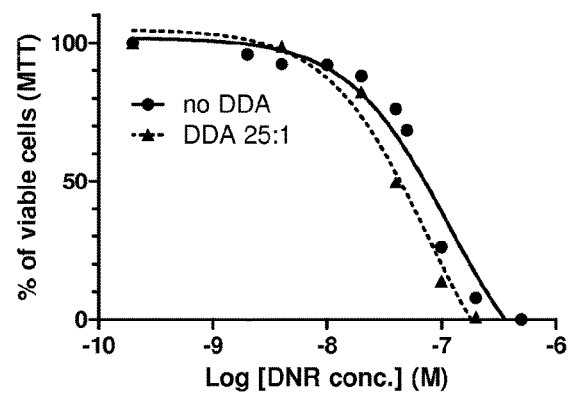
FIG. 11A is a curve diagram showing the effect of the combination of Dendrogenin A and Daunorubicin (25:1 molecular ratio) on cell viability in the drug sensitive cancer cell line MV4-11.
FIG. 11B is an isobologram representation showing the synergistic effect of the combination of Dendrogenin A and Daunorubicin on cell viability of the drug sensitive cancer cell line MV4-11.
FIG. 11C is a curve diagram showing the combination index (CI) values on cell viability in the drug sensitive cancer cell line MV4-11 for the combination of Dendrogenin A and Daunorubicin.
Figure 11:
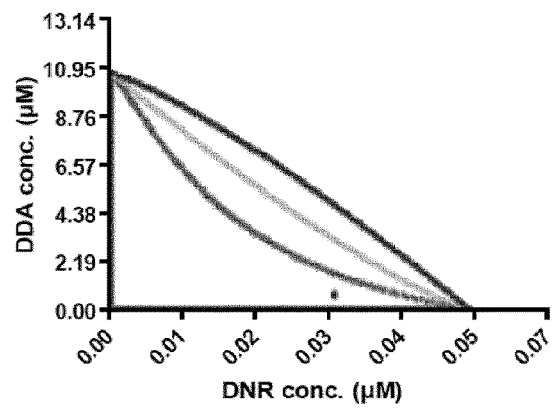
Figure 11:
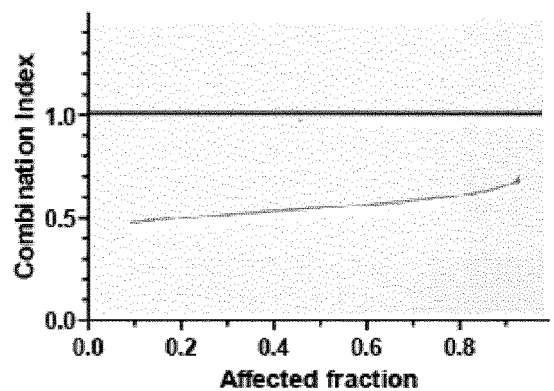

Association of Dendrogenin A and daunorubicin synergistically reduces viability of the drug-sensitive cell line MV4-11, as shown in FIGS. 11A, 11B and 11C.

Example 12

Synergistic Activity of the Association Dendrogenin A/Cytarabine on the Cytotoxic Drug-Sensitive Cell Line KG1

KG1 cells were seeded in 96-well plates (50 000 cells/well). Cells were treated just after seeding with increasing doses of Dendrogenin A and Cytarabine, for 48 hours. Cell viability was determined with MTT assay as described in example 1.

Figure 12:
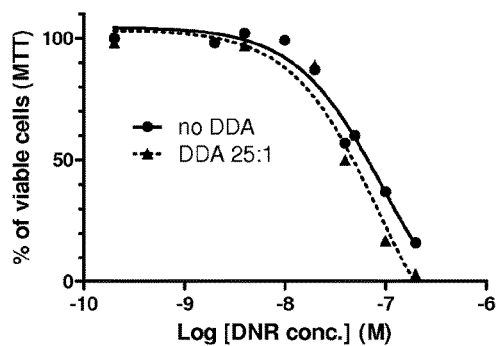
FIG. 12A is a curve diagram showing the effect of the combination of Dendrogenin A and Cytarabine (5:1 molecular ratio) on cell viability of the drug sensitive cancer cell line KG1.
FIG. 12B is an isobologram representation showing the synergistic effect of the combination of Dendrogenin A and Cytarabine on cell viability of drug sensitive cancer cell line KG1.
FIG. 12C is a curve diagram showing the combination index (CI) values on cell viability of the drug sensitive cancer cell line KG1 for the combination of Dendrogenin A and Cytarabine.
Figure 12:
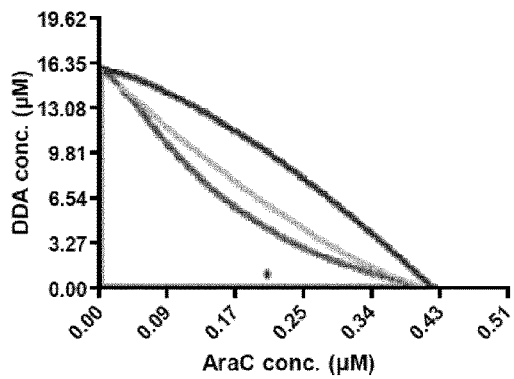
Figure 12:
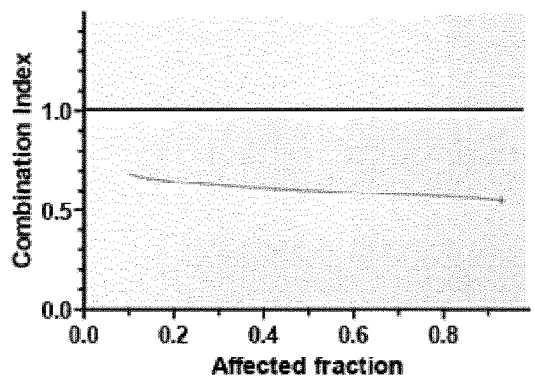

Association of Dendrogenin A and cytarabine synergistically reduces viability of the drug-sensitive cell line KG1, as shown in FIG. 12.

Example 13

Synergistic Activity of the Association Dendrogenin A/Cytarabine on the Cytotoxic Drug-Sensitive Cell Line MV4-11

MV4-11 cells were seeded in 96-well plates (50 000 cells/well). Cells were treated just after seeding with increasing doses of Dendrogenin A and Cytarabine, for 48 hours. Cell viability was determined with MTT assay as described in example 1.

Figure 13:
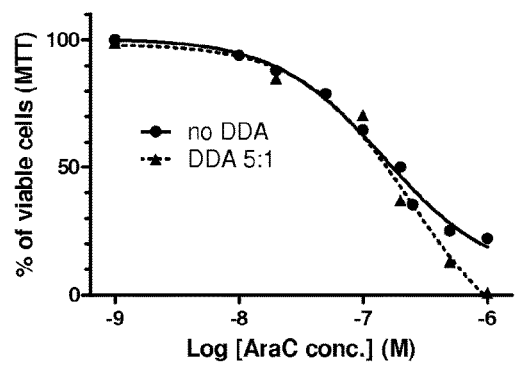
FIG. 13A is a curve diagram showing the effect of the combination of Dendrogenin A and Cytarabine (5:1 molecular ratio) on cell viability in the drug sensitive cancer cell line MV4-11.
FIG. 13B is an isobologram representation showing the synergistic effect of the combination of Dendrogenin A and Cytarabine on cell viability of drug sensitive cancer cell line MV4-11.
FIG. 13C is a curve diagram showing the combination index (CI) values on cell viability in the drug sensitive cancer cell line MV4-11 for the combination of Dendrogenin A and Cytarabine.
Figure 13:
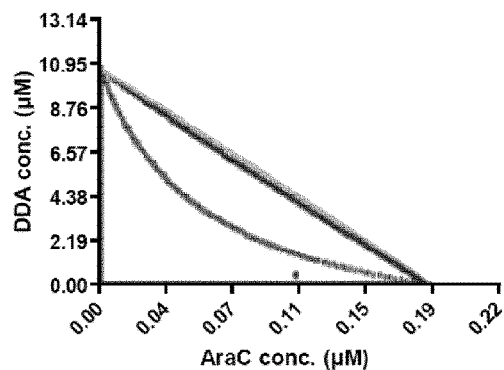
Figure 13:
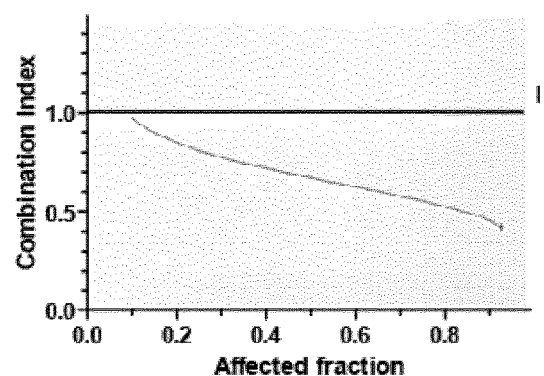

Association of Dendrogenin A and cytarabin synergistically reduces viability of the drug-sensitive cell line MV4-11, as shown in FIGS. 13a, 13b, 13c.

Example 14

Synergistic Activity of the Association Dendrogenin A/5-Fluorouracil on the Cytotoxic Drug-Sensitive Cell Line HL60

HL60 cells were seeded in 96-well plates (50 000 cells/well). Cells were treated just after seeding with increasing doses of Dendrogenin A and 5-Fluorouracil, for 48 hours. Cell viability was determined with MTT assay as described in example 1.

Figure 14:
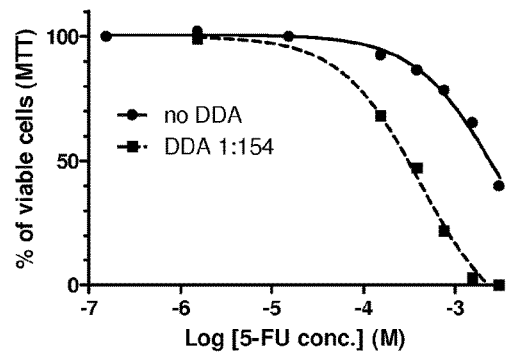
FIG. 14A is a curve diagram showing the effect of the combination of Dendrogenin A and 5-fluorouracil (1:154 molecular ratio) on cell viability of the drug sensitive cancer cell line HL60.
FIG. 14B is an isobologram representation showing the synergistic effect of the combination of Dendrogenin A and 5-Fluorouracil on cell viability of drug sensitive cancer cell line HL60.
FIG. 14C is a curve diagram showing the combination index (CI) values on cell viability in the cancer cell line HL60 for the combination of Dendrogenin A and 5-Fluorouracil.
Figure 14:
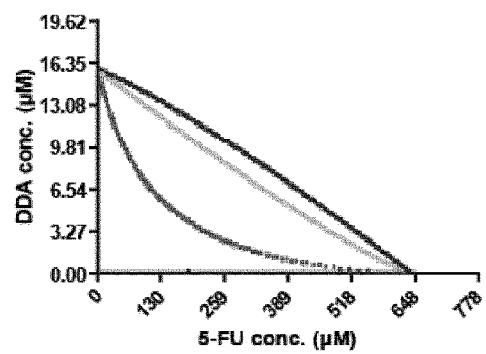
Figure 14:
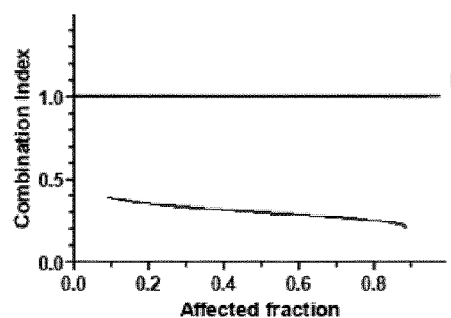

Association of Dendrogenin A and 5-fluorouracil synergistically reduces viability of the drug-sensitive cell line HL60, as shown in FIGS. 14a, 14b and 14c.

Example 15

Synergistic Activity of the Association Dendrogenin A/5-Fluorouracil on the Cytotoxic Drug-Sensitive Cell Line KG1

KG1 cells were seeded in 96-well plates (50 000 cells/well). Cells were treated just after seeding with increasing doses of Dendrogenin A and 5-Fluorouracil, for 48 hours. Cell viability was determined with MTT assay as described in example 1.

Figure 15:
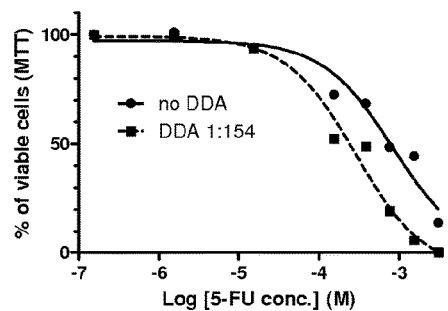
FIG. 15A is a curve diagram showing the effect of the combination of Dendrogenin A and 5-fluorouracil (1:154 molecular ratio) on cell viability of the cancer cell line KG1.
FIG. 15B is an isobologram representation showing the synergistic effect of the combination of Dendrogenin A and 5-Fluorouracil on cell viability of drug sensitive cancer cell line KG1.
FIG. 15C is a curve diagram showing the combination index (CI) values on cell viability in the drug sensitive cancer cell line KG1 for the combination of Dendrogenin A and 5-Fluorouracil.
Figure 15:
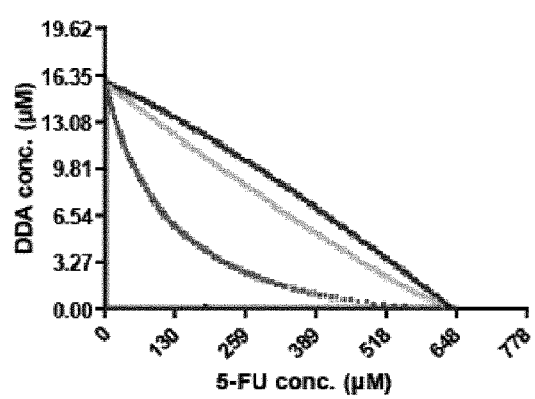
Figure 15:
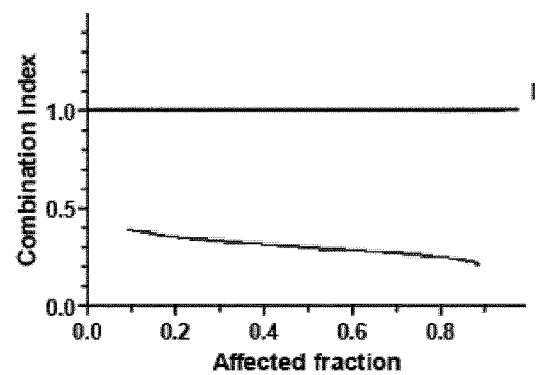

Association of Dendrogenin A and 5-fluorouracile synergistically reduces viability of the drug-sensitive cell line KG1, as shown in FIGS. 15a, 15b and 15c.

Example 16

Synergistic Activity of the Association Dendrogenin A/5-Fluorouracil on the Chemoresistant Cell Line KG1a KG1a cells were seeded in 96-well plates (50 000 cells/well). Cells were treated just after seeding with increasing doses of Dendrogenin A and 5-Fluorouracil, for 48 hours. Cell viability was determined with MTT assay as described in example 1.

Figure 16:
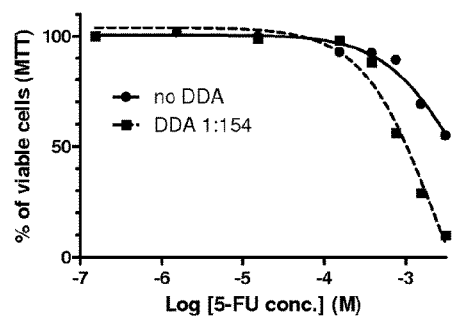
Figure 16:
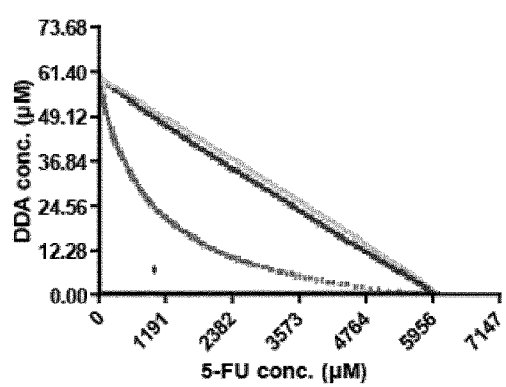
Figure 16:
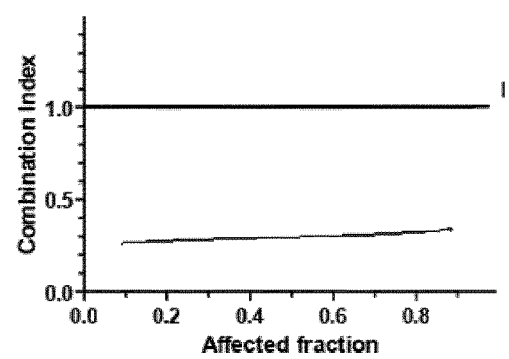

Association of Dendrogenin A and 5-fluorouracile synergistically reduces viability of the chemoresistant cell line KG1a, as shown in FIGS. 16a, 16b and 16c.

Example 17

Synergistic Activity of the Association Dendrogenin A/Cisplatin on the Cytotoxic Drug-Sensitive Cell Line HL60

HL60 cells were seeded in 96-well plates (50 000 cells/well). Cells were treated just after seeding with increasing doses of Dendrogenin A and Cisplatin, for 48 hours. Cell viability was determined with MTT assay as described in example 1.

Figure 17:
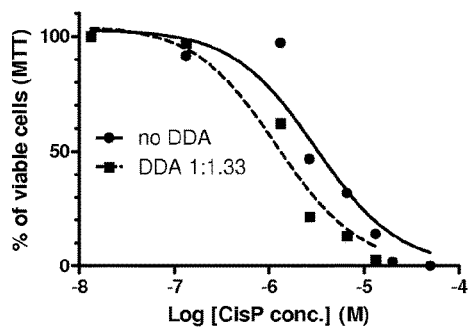
FIG. 17A is a curve diagram showing the effect of the combination of Dendrogenin A and Cisplatin (1:1.33 molecular ratio) on cell viability of the drug sensitive cancer cell line HL60.
FIG. 17B is an isobologram representation showing the synergistic effect of the combination of Dendrogenin A and Cisplatin on cell viability of drug sensitive cancer cell line HL60.
FIG. 17C is a curve diagram showing the combination index (CI) values on cell viability in the drug sensitive cancer cell line HL60 for the combination of Dendrogenin A and Cisplatin.
Figure 17:
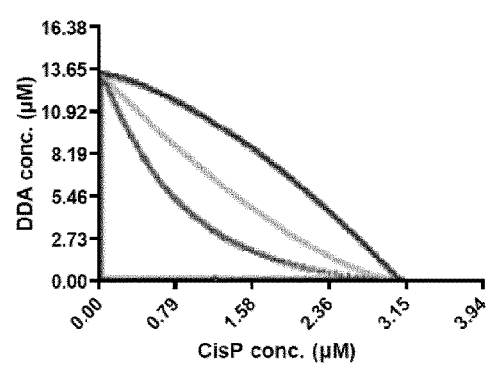
Figure 17:
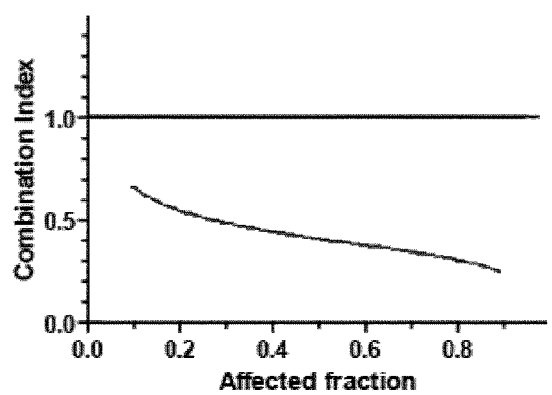

Association of Dendrogenin A and cisplatin synergistically reduces viability of the drug-sensitive cell line HL60, as shown in FIGS. 17a, 17b and 17c.

Example 18

Synergistic Activity of the Association Dendrogenin A/Cisplatin on the Cytotoxic Drug-Sensitive Cell Line KG1

KG1 cells were seeded in 96-well plates (50 000 cells/well). Cells were treated just after seeding with increasing doses of Dendrogenin A and Cisplatin, for 48 hours. Cell viability was determined with MTT assay as described in example 1.

Figure 18:
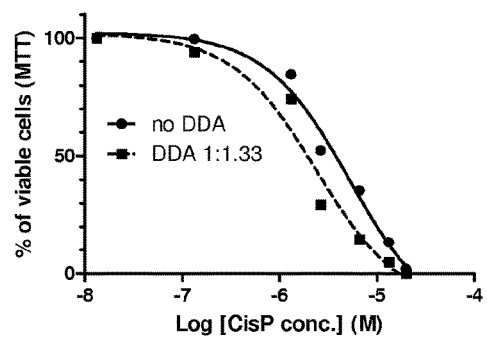
FIG. 18A is a curve diagram showing the effect of the combination of Dendrogenin A and Cisplatin (1:1.33 molecular ratio) on cell viability of the drug sensitive cancer cell line KG1.
FIG. 18B is an isobologram representation showing the synergistic effect of the combination of Dendrogenin A and Cisplatin on cell viability of drug sensitive cancer cell line KG1.
FIG. 18C is a curve diagram showing the combination index (CI) values on cell viability in the drug sensitive cancer cell line KG1 for the combination of Dendrogenin A and Cisplatin.
Figure 18:
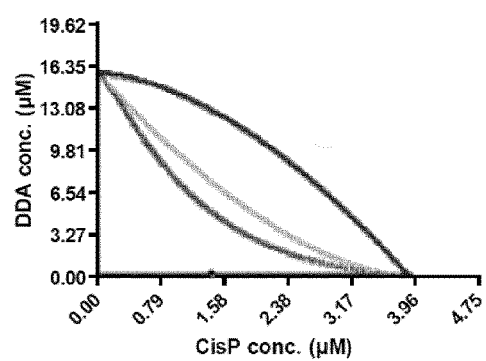
Figure 18:
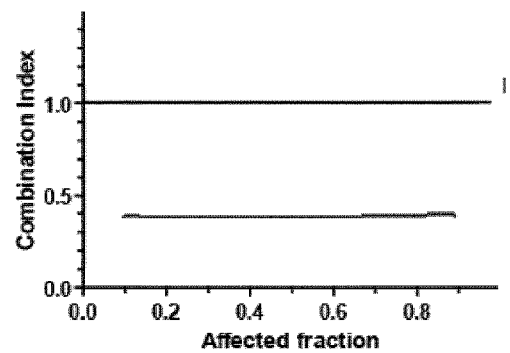

Association of Dendrogenin A and cisplatin synergistically reduces viability of the drug-sensitive cell line KG1, as shown in FIGS. 18a, 18b and 18c.

Example 19

Synergistic Activity of the Association Dendrogenin A/Cisplatin on the Chemoresistant Cell Line KG1a KG1a cells were seeded in 96-well plates (50 000 cells/well). Cells were treated just after seeding with increasing doses of Dendrogenin A and Cisplatin, for 48 hours. Cell viability was determined with MTT assay as described in example 1.

Figure 19:
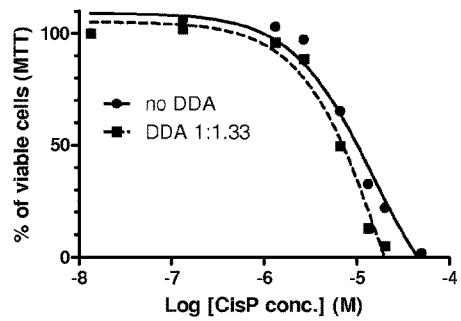
Figure 19:
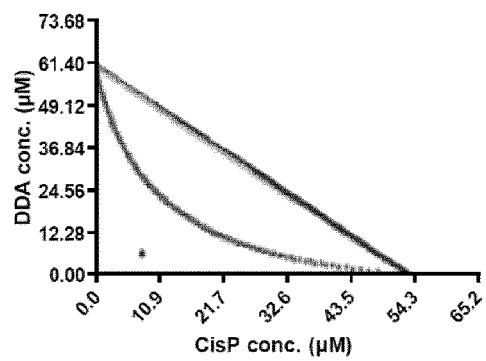
Figure 19:
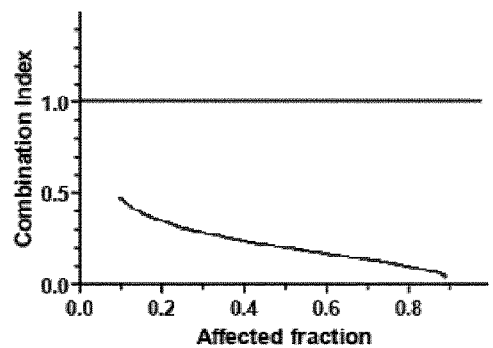

Association of Dendrogenin A and cisplatin synergistically reduces viability of the chemoresistant cell line KG1a, as shown in FIGS. 19a, 19b and 19c.

Example 20

Synergistic Activity of the Association Dendrogenin A/Bortezomib on the Cytotoxic Drug-Sensitive Cell Line KG1

KG1 cells were seeded in 96-well plates (50 000 cells/well). Cells were treated just after seeding with increasing doses of Dendrogenin A and Bortezomib, for 48 hours. Cell viability was determined with MTT assay as described in example 1.

Figure 20:
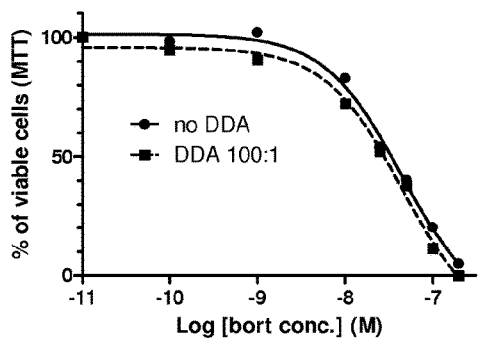
FIG. 20A is a curve diagram showing the effect of the combination of Dendrogenin A and Bortezomib (100:1 molecular ratio) on cell viability of the drug sensitive cancer cell line KG1.
FIG. 20B is an isobologram representation showing the synergistic effect of the combination of Dendrogenin A and Bortezomib on cell viability of drug sensitive cancer cell line KG1.
FIG. 20C is a curve diagram showing the combination index (CI) values on cell viability in the drug sensitive cancer cell line KG1 for the combination of Dendrogenin A and Bortezomib.
Figure 20:
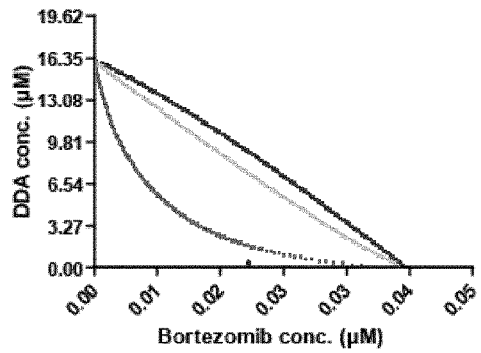
Figure 20:
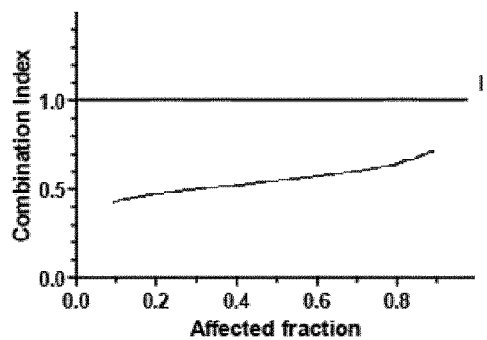

Association of Dendrogenin A and Bortezomib synergistically reduces viability of the drug-sensitive cell line KG1, as shown in FIGS. 20a, 20b and 20c.

Example 21

Synergistic Activity of the Association Dendrogenin A/Bortezomib on the Cytotoxic Drug-Sensitive Cell Line HL60

HL60 cells were seeded in 96-well plates (50 000 cells/well). Cells were treated just after seeding with increasing doses of Dendrogenin A and Bortezomib, for 48 hours. Cell viability was determined with MTT assay as described in example 1.

Figure 21:
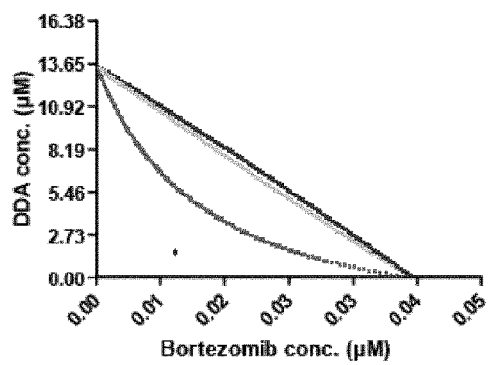
FIG. 21A is a curve diagram showing the effect of the combination of Dendrogenin A and Bortezomib (100:1 molecular ratio) on cell viability of the drug sensitive cancer cell line HL60.
FIG. 21B is an isobologram representation showing the synergistic effect of the combination of Dendrogenin A and Bortezomib on cell viability of drug sensitive cancer cell line HL60.
FIG. 21C is a curve diagram showing the combination index (CI) values on cell viability in the drug sensitive cancer cell line HL60 for the combination of Dendrogenin A and Bortezomib.
Figure 21:
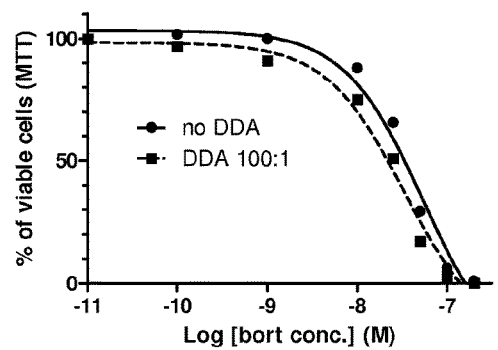
Figure 21:
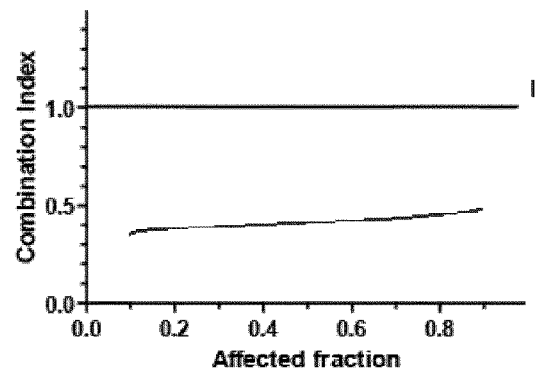

Association of Dendrogenin A and Bortezomib synergistically reduces viability of the drug-sensitive cell line HL60, as shown in FIG. 21.

Example 22

Synergistic Activity of the Association Dendrogenin A/Arsenic Trioxide on the Cytotoxic Drug-Sensitive Cell Line KG1

KG1 cells were seeded in 96-well plates (50 000 cells/well). Cells were treated just after seeding with increasing doses of Dendrogenin A and arsenic trioxide, for 48 hours. Cell viability was determined with MTT assay as described in example 1.

Figure 22:
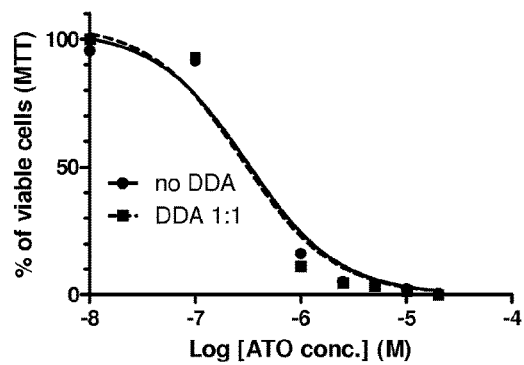
FIG. 22A is a curve diagram showing the effect of the combination of Dendrogenin A and arsenic trioxide (1:1 molecular ratio) on cell viability of the drug sensitive cancer cell line KG1.
FIG. 22B is an isobologram representation showing the synergistic effect of the combination of Dendrogenin A and arsenic trioxide on cell viability of drug sensitive cancer cell line KG1.
FIG. 22C is a curve diagram showing the combination index (CI) values on cell viability in the drug sensitive cancer cell line KG1 for the combination of Dendrogenin A and arsenic trioxide.
Figure 22:
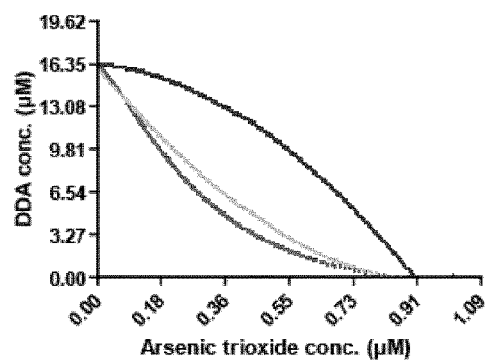
Figure 22:
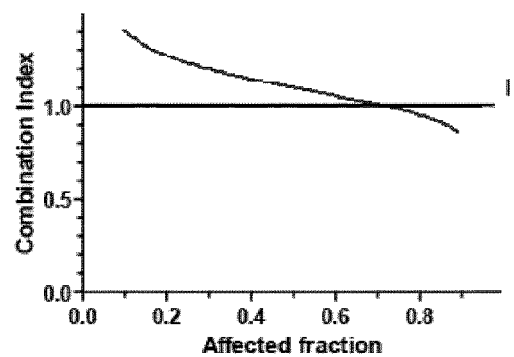

Association of Dendrogenin A and arsenic trioxide synergistically reduces viability of the drug-sensitive cell line KG1, as shown in FIGS. 22a, 22b and 22c. Synergy exists only when most cancer cells are affected, so a good knowledge of the sensitivity of the tumor to arsenic trioxide and Dendrogenin A will be needed to be in the optimal synergistic range.

Example 23

Synergistic Activity of the Association Dendrogenin A/Arsenic Trioxide on the Cytotoxic Drug-Sensitive Cell Line HL60

HL60 cells were seeded in 96-well plates (50 000 cells/well). Cells were treated just after seeding with increasing doses of Dendrogenin A and arsenic trioxide, for 48 hours. Cell viability was determined with MTT assay as described in example 1.

Figure 23:
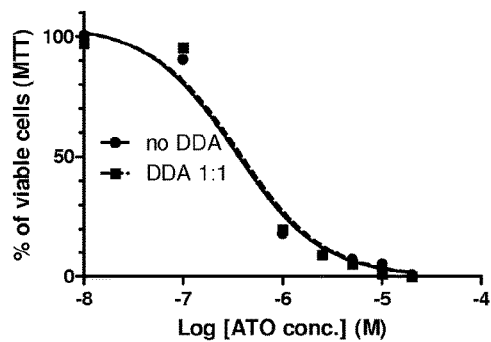
FIG. 23A is a curve diagram showing the effect of the combination of Dendrogenin A and arsenic trioxide (1:1 molecular ratio) on cell viability of the drug sensitive cancer cell line HL60.
FIG. 23B is an isobologram representation showing the synergistic effect of the combination of Dendrogenin A and arsenic trioxide on cell viability of drug sensitive cancer cell line HL60.
FIG. 23C is a curve diagram showing the combination index (CI) values on cell viability in the drug sensitive cancer cell line HL60 for the combination of Dendrogenin A and arsenic trioxide.
Figure 23:
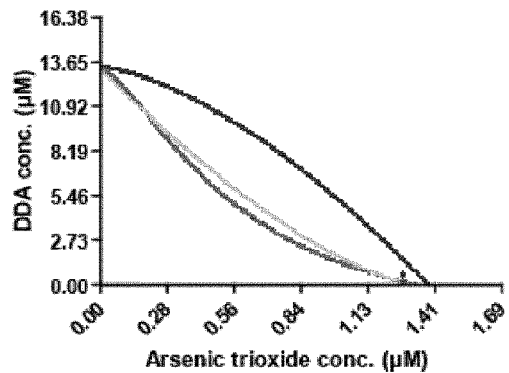
Figure 23:
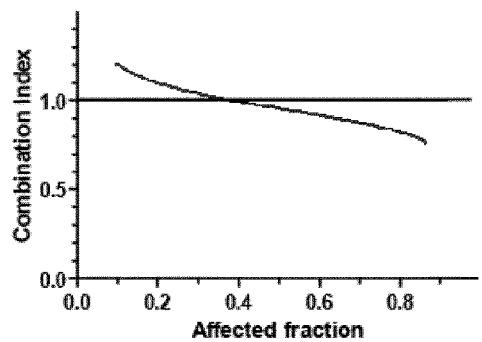

Association of Dendrogenin A and arsenic trioxide synergistically reduces viability of the drug-sensitive cell line HL60, as shown in FIGS. 23a, 23b and 23c. Synergy exists only when most cancer cells are affected, so a good knowledge of the sensitivity of the tumor to arsenic trioxide and Dendrogenin A will be needed to be in the optimal synergistic range.

Example 24

Synergistic Activity of the Association Dendrogenin A/all-Trans Retinoic Acid on the Cytotoxic Drug-Sensitive Cell Line KG1

KG1 cells were seeded in 96-well plates (50 000 cells/well). Cells were treated just after seeding with increasing doses of Dendrogenin A and all-trans retinoic acid, for 48 hours. Cell viability was determined with MTT assay as described in example 1.

Figure 24:
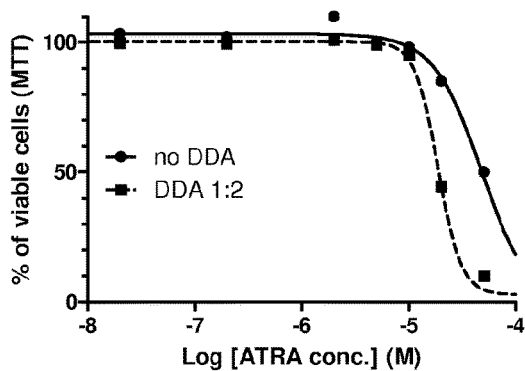
FIG. 24A is a curve diagram showing the effect of the combination of Dendrogenin A and ATRA (1:2 molecular ratio) on cell viability of the drug sensitive cancer cell line KG1.
FIG. 24B is an isobologram representation showing the synergistic effect of the combination of Dendrogenin A and ATRA on cell viability of drug sensitive cancer cell line KG1.
FIG. 24C is a curve diagram showing the combination index (CI) values on cell viability in the drug sensitive cancer cell line KG1 for the combination of Dendrogenin A and ATRA.
Figure 24:
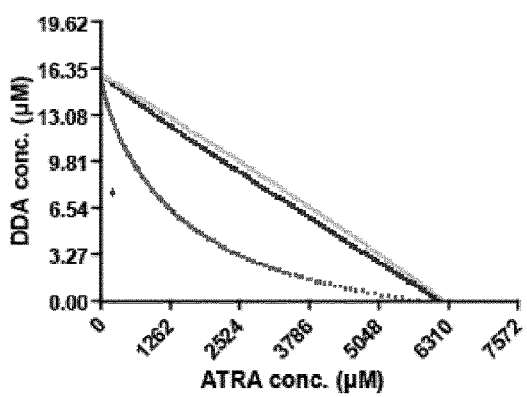
Figure 24:
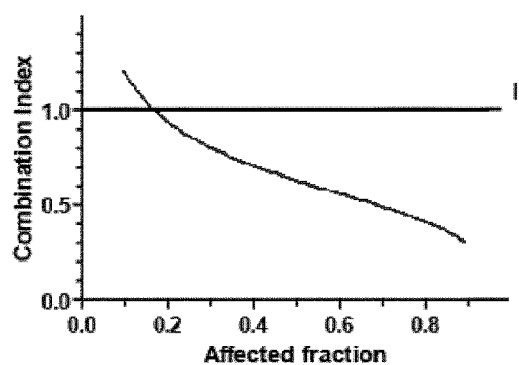

Association of Dendrogenin A and all-trans retinoic acid synergistically reduces viability of the drug-sensitive cell line KG1, as shown in FIGS. 24a, 24b and 24c.

Example 25

Synergistic Activity of the Association Dendrogenin A/All-Trans Retinoic Acid on the Cytotoxic Drug-Sensitive Cell Line HL60

HL60 cells were seeded in 96-well plates (50 000 cells/well). Cells were treated just after seeding with increasing doses of Dendrogenin A and all-trans retinoic acid, for 48 hours. Cell viability was determined with MTT assay as described in example 1.

Figure 25:
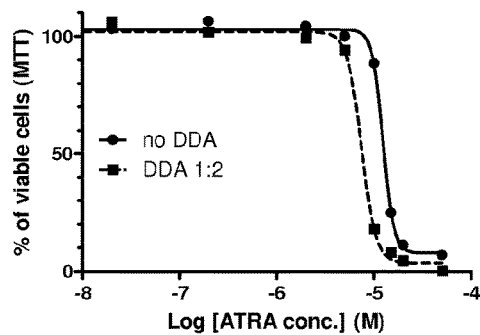
FIG. 25A is a curve diagram showing the effect of the combination of Dendrogenin A and ATRA (1:2 molecular ratio) on cell viability of the drug sensitive cancer cell line HL60.
FIG. 25B is an isobologram representation showing the synergistic effect of the combination of Dendrogenin A and ATRA on cell viability of drug sensitive cancer cell line HL60.
FIG. 25C is a curve diagram showing the combination index (CI) values on cell viability in the drug sensitive cancer cell line HL60 for the combination of Dendrogenin A and ATRA.
Figure 25:
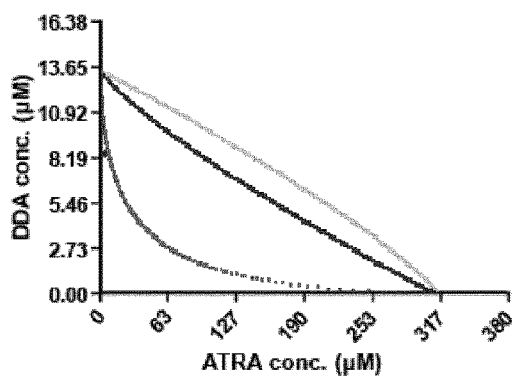
Figure 25:
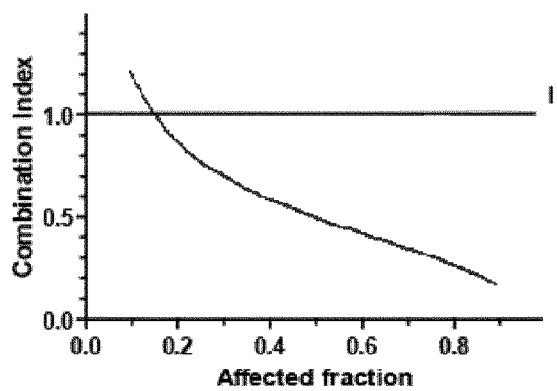

Association of Dendrogenin A and all-trans retinoic acid synergistically reduces viability of the drug-sensitive cell line HL60, as shown in FIGS. 25a, 25b and 25c.

Example 26

Synergistic Activity of the Association Dendrogenin A/5-Fluorouracil on the Drug-Sensitive Cell Line MCF-7

MCF-7 cells were seeded in 96-well plates (5 000 cells/well). Cells were treated just after seeding with increasing doses of Dendrogenin A and 5-Fluorouracil, for 48 hours. Cell viability was determined with MTT assay as described in example 1.

Figure 26:
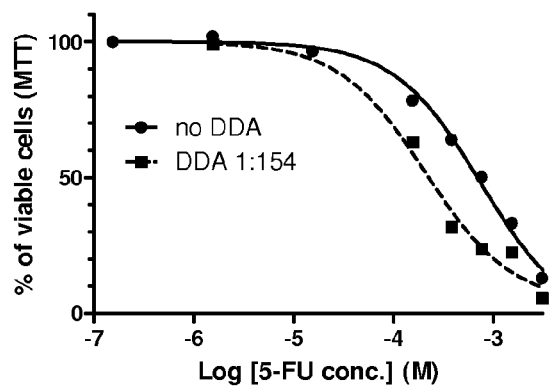
FIG. 26A is a curve diagram showing the effect of the combination of Dendrogenin A and 5-fluorouracil (1:154 molecular ratio) on cell viability of the drug sensitive cancer cell line Mcf7.
FIG. 26B is an isobologram representation showing the synergistic effect of the combination of Dendrogenin A and 5-fluorouracil on cell viability of drug sensitive cancer cell line Mcf7.
FIG. 26C is a curve diagram showing the combination index (CI) values on cell viability in the drug sensitive cancer cell line Mcf7 for the combination of Dendrogenin A and 5-fluorouracil.
Figure 26:
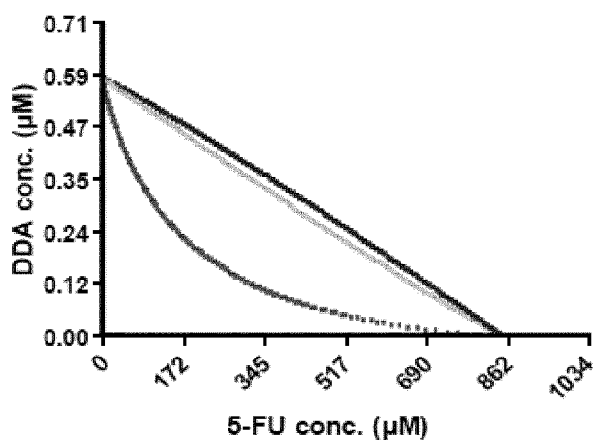
Figure 26:
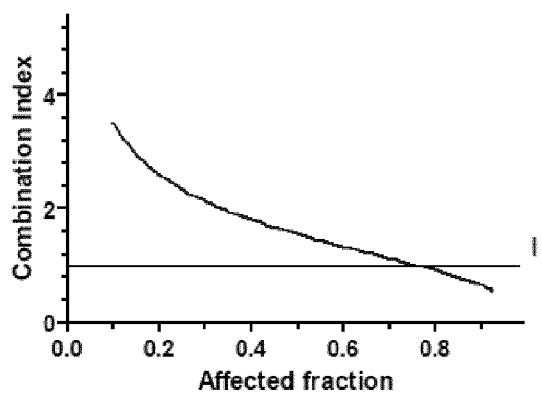

Association of Dendrogenin A and 5-Fluorouracil synergistically reduces viability of the drug-sensitive cell line MCF-7, as shown in FIGS. 26a, 26b and 26c. Synergy exists only when most cancer cells are affected, so a good knowledge of the sensitivity of the tumor to 5-Fluorouracil and Dendrogenin A will be needed to be in the optimal synergistic range.

Example 27

Synergistic Activity of the Association Dendrogenin A/5-Fluorouracil on the Drug-Sensitive Cell Line SK-MEL-28

SK-MEL-28 cells were seeded in 96-well plates (5 000 cells/well). Cells were treated just after seeding with increasing doses of Dendrogenin A and 5-Fluorouracil, for 48 hours. Cell viability was determined with MTT assay as described in example 1.

Figure 27:
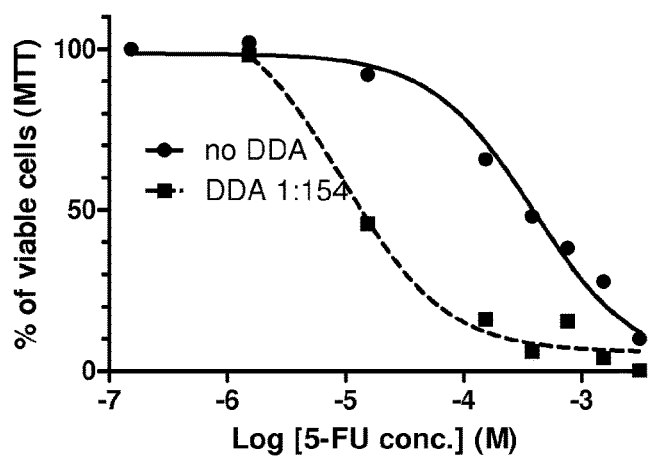
FIG. 27A is a curve diagram showing the effect of the combination of Dendrogenin A and 5-fluorouracil (1:154 molecular ratio) on cell viability of the drug sensitive cancer cell line SKMel28.
FIG. 27B is an isobologram representation showing the synergistic effect of the combination of Dendrogenin A and 5-fluorouracil on cell viability of drug sensitive cancer cell line SKMel28.
FIG. 27C is a curve diagram showing the combination index (CI) values on cell viability in the drug sensitive cancer cell line SKMel28 for the combination of Dendrogenin A and 5-fluorouracil.
Figure 27:
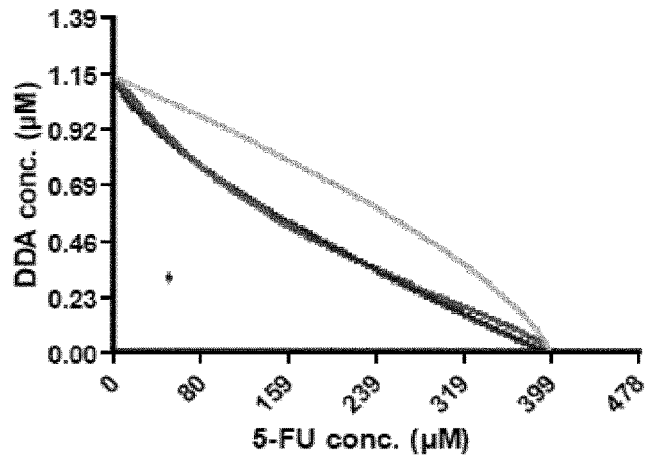
Figure 27:
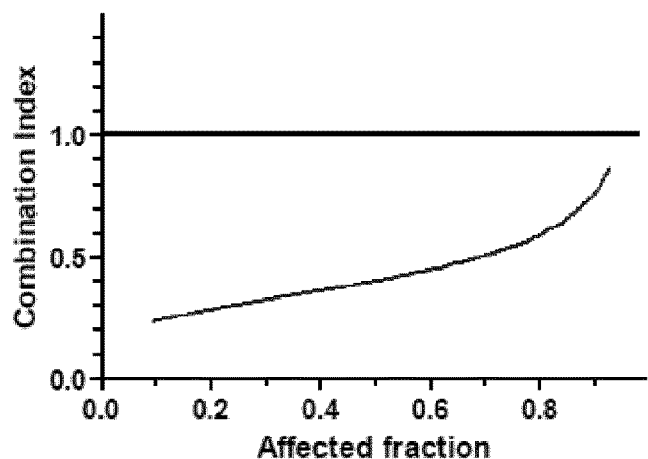

Association of Dendrogenin A and 5-Fluorouracil synergistically reduces viability of the drug-sensitive cell line SK-MEL-28, as shown in FIGS. 27a, 27b and 27c.

Example 28

Synergistic Activity of the Association Dendrogenin A/CisPlatin on the Drug-Resistant Cell Line MCF-7

MCF-7 cells were seeded in 96-well plates (5 000 cells/well). Cells were treated just after seeding with increasing doses of Dendrogenin A and CisPlatin, for 48 hours. Cell viability was determined with MTT assay as described in example 1.

Figure 28:
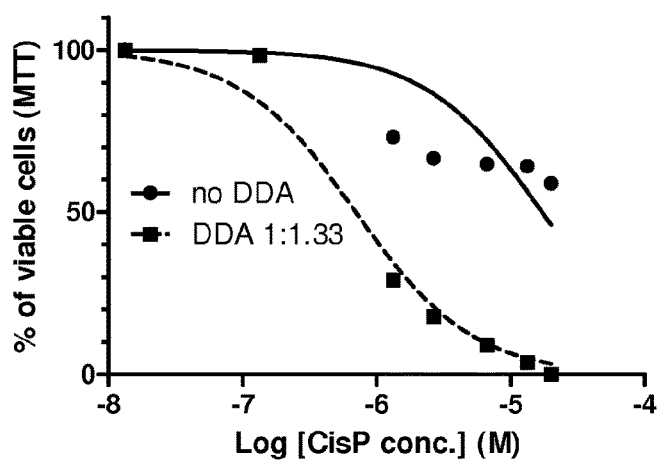
FIG. 28A is a curve diagram showing the effect of the combination of Dendrogenin A and CisPlatin (1:1.33 molecular ratio) on cell viability of the drug resistant cancer cell line Mcf7.
FIG. 28B is an isobologram representation showing the synergistic effect of the combination of Dendrogenin A and CisPlatin on cell viability of drug resistant cancer cell line Mcf7.
FIG. 28C is a curve diagram showing the combination index (CI) values on cell viability in the drug resistant cancer cell line Mcf7 for the combination of Dendrogenin A and CisPlatin.
Figure 28:
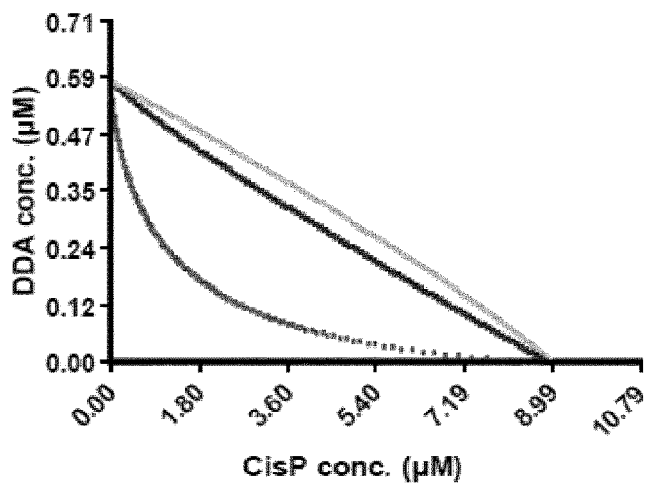
Figure 28:
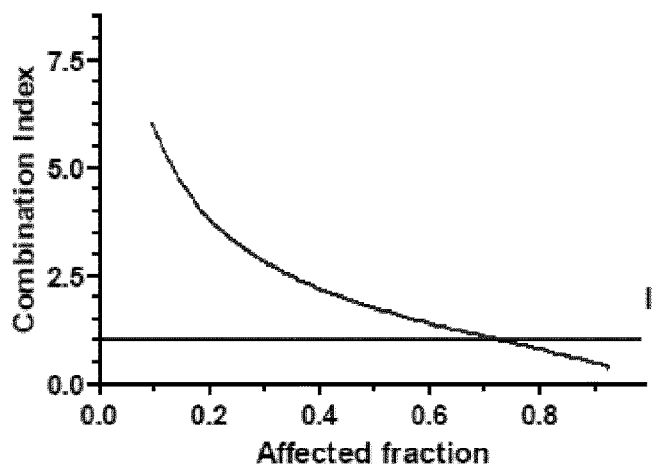

Association of Dendrogenin A and CisPlatin synergistically reduces viability of the drug-resistant cell line MCF-7, as shown in FIGS. 28a, 28b and 28c. Synergy exists only when most cancer cells are affected, so a good knowledge of the sensitivity of the tumor to CisPlatin and Dendrogenin A will be needed to be in the optimal synergistic range.

Example 29

Synergistic Activity of the Association Dendrogenin A/CisPlatin on the Drug-Resistant Cell Line SK-MEL-28

SK-MEL-28 cells were seeded in 96-well plates (5 000 cells/well). Cells were treated just after seeding with increasing doses of Dendrogenin A and CisPlatin, for 48 hours. Cell viability was determined with MTT assay as described in example 1.

Figure 29:
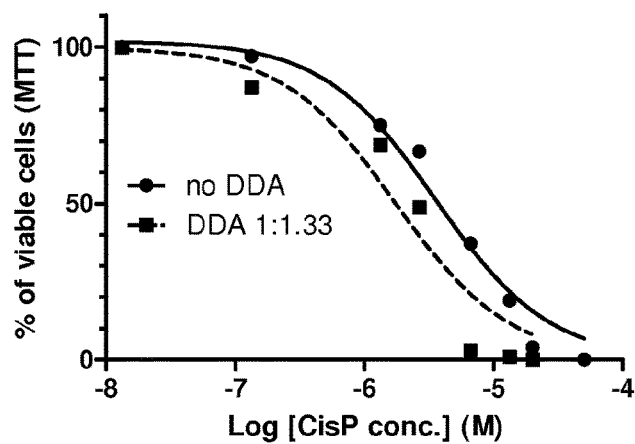
FIG. 29A is a curve diagram showing the effect of the combination of Dendrogenin A and CisPlatin (1:1.33 molecular ratio) on cell viability of the drug sensitive cancer cell line SKMel28.
FIG. 29B is an isobologram representation showing the synergistic effect of the combination of Dendrogenin A and CisPlatin on cell viability of drug sensitive cancer cell line SKMel28.
FIG. 29C is a curve diagram showing the combination index (CI) values on cell viability in the drug sensitive cancer cell line SKMel28 for the combination of Dendrogenin A and CisPlatin.
Figure 29:
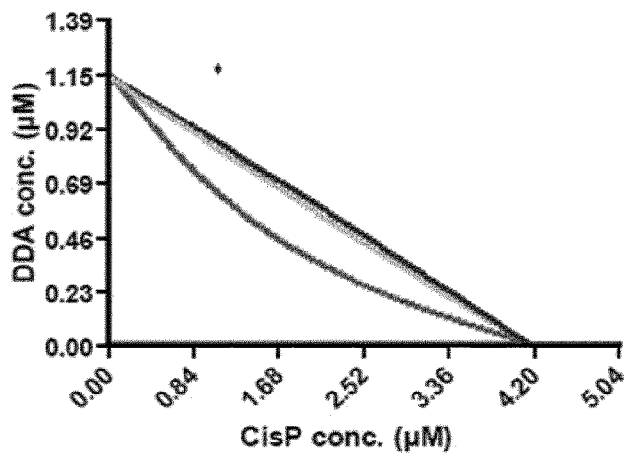
Figure 29:
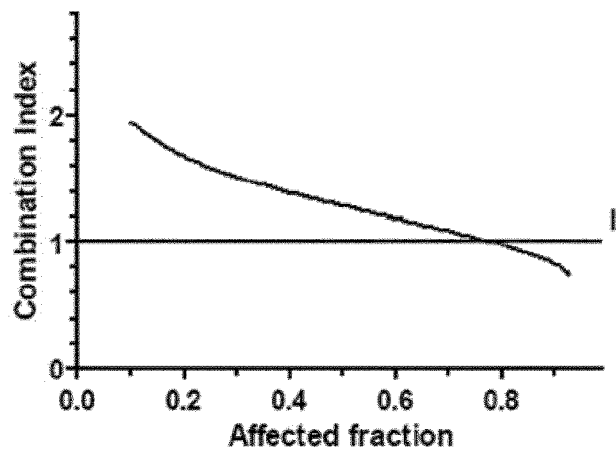

Association of Dendrogenin A and CisPlatin synergistically reduces viability of the drug-resistant cell line SK-MEL-28, as shown in FIGS. 29a, 29b and 29c. Synergy exists only when most cancer cells are affected, so a good knowledge of the sensitivity of the tumor to CisPlatin and Dendrogenin A will be needed to be in the optimal synergistic range.

Example 30

Figure 30:
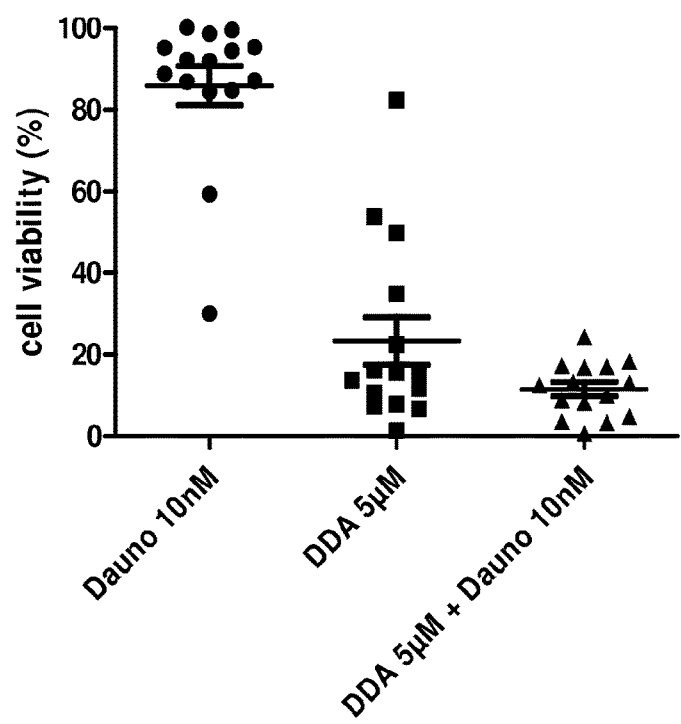
FIG. 30 is a scatter plot representation showing the effect of the combination of Dendrogenin A and Daunorubicin on cell viability of kariotipically and phenotipically distinct Acute Myeloid Leukemia from patients.

Dendrogenin A Increases the Cytotoxic Sensitivity to Daunorubicin of Kariotypically and Phenotypically Different AML Patient Samples In a 6-microwell plate were seeded $0.5.10^6$ patient cells. The same day, Solvant vehicle or different concentrations of Dendrogenin A (final concentrations: 5 μM) alone or in combination with Daunorubicin (final concentration: 10 nM) were added into the well. After 48 hours of incubation, the cells suspensions were centrifuged and washed with PBS and cell pellets were resuspended in a labeling solution containing Annexin V-FitC and 7-AAD as described in the kit protocol (Annexin V-FitC/7-AAD staining kit, Roche Applied Science). Cells were then incubated for 15 minutes at room temperature in the dark and analyzed by Facs Flow cytometry. The results are shown in FIG. 30.

This example shows on one hand that Dendrogenin A is able to induce high or moderate cell death rate of tumor cells resistant to Daunorubicin and on the other hand that a combination of Dendrogenin A and Daunorubicin is able to induce total cell death rate of the same tumor cells.

The invention claimed is:

1. A method for treating a cancer acute myeloid leukemia which is chemoresistant to an antineoplastic agent in a patient in need thereof comprising administering to said patient 5α-hydroxy-6β-[2-(1H-imidazol-4-yl)ethylamino]cholestan-3β-ol or a pharmaceutically acceptable salt thereof and said antineoplastic agent, wherein said antineoplastic agent is cytarabine.

2. The method according to claim 1, wherein the acute myeloid leukemia is chemoresistant to said antineoplastic agent when not administered in combination with 5α-hydroxy-6β-[2-(1H-imidazol-4-yl)ethylamino]cholestan-3β-ol or a pharmaceutically acceptable salt thereof to said patient.

3. The method according to claim 1, wherein a dose of said antineoplastic agent is administered to said patient in combination with 5α-hydroxy-6β-[2-(1H-imidazol-4-yl)ethylamino]cholestan-3β-ol or a pharmaceutically acceptable salt thereof and said dose is lower than the dose of antineoplastic agent when not administered in combination with 5α-hydroxy-6β-[2-(1H-imidazol-4-yl)ethylamino]cholestan-3β-ol or a pharmaceutically acceptable salt thereof to said patient.

4. The method according to claim 1, wherein 5α-hydroxy-6β-[2-(1H-imidazol-4-yl)ethylamino]cholestan-3β-ol or a pharmaceutically acceptable salt thereof and the antineoplastic agent are simultaneously administered to said patient.

5. The method according to claim 1, wherein 5α-hydroxy-6β-[2-(1H-imidazol-4-yl)ethylamino]cholestan-3β-ol or a pharmaceutically acceptable salt thereof and the antineoplastic agent are sequentially administered to said patient.

6. The method according to claim 5, wherein 5α-hydroxy-6β-[2-(1H-imidazol-4-yl)ethylamino]cholestan-3β-ol or a pharmaceutically acceptable salt thereof is administered prior to the antineoplastic agent.

7. A method for restoring the sensibility of a tumor which is chemoresistant to an antineoplastic agent in a patient having acute myeloid leukemia, consisting essentially of administering to said patient a therapeutically effective amount of 5α-hydroxy-6β-[2-(1H-imidazol-4-yl)ethylamino]cholestan-3β-ol or a pharmaceutically acceptable salt thereof and a therapeutically effective amount of said antineoplastic agent, wherein said antineoplastic agent is cytarabine.

8. A method for increasing the sensibility of a tumor to an antineoplastic agent in a patient having acute myeloid leukemia comprising administering to said patient 5α-hydroxy-6β-[2-(1H-imidazol-4-yl)ethylamino]cholestan-3β-ol or a pharmaceutically acceptable salt thereof in an amount sufficient to increase the sensibility of said tumor to said antineoplastic agent, wherein said antineoplastic agent is cytarabine.

9. The method according to claim 8, wherein a dose of the antineoplastic agent is administered to said patient in combination with 5α-hydroxy-6β-[2-(1H-imidazol-4-yl)ethylamino]cholestan-3β-ol or a pharmaceutically acceptable salt thereof and said dose is lower than the dose of antineoplastic agent when not administered in combination with 5α-hydroxy-6β-[2-(1H-imidazol-4-yl)ethylamino]cholestan-3β-ol or a pharmaceutically acceptable salt thereof to said patient.

10. A method for treating a cancer which is chemoresistant to an antineoplastic agent in a patient in need thereof comprising administering to said patient 5α-hydroxy-6β-[2-(1H-imidazol-4-yl)ethylamino]cholestan-3β-ol or a pharmaceutically acceptable salt thereof and said antineoplastic agent, wherein said cancer is selected from the group consisting of breast cancer, melanoma, lung cancer, embryonal carcinoma, neuroblastoma, glioma, colon cancer, and gastrointestinal cancer and wherein said antineoplastic agent is daunorubicine.

11. The method according to claim 10, wherein the cancer is chemoresistant to said antineoplastic agent when not administered in combination with 5α-hydroxy-6β-[2-(1H-imidazol-4-yl)ethylamino]cholestan-3β-ol or a pharmaceutically acceptable salt thereof to said patient.

12. The method according to claim 10, wherein a dose of said antineoplastic agent is administered to said patient in combination with 5α-hydroxy-6β-[2-(1H-imidazol-4-yl)ethylamino]cholestan-3β-ol or a pharmaceutically acceptable salt thereof and said dose is lower than the dose of antineoplastic agent when not administered in combination with 5α-hydroxy-6β-[2-(1H-imidazol-4-yl)ethylamino]cholestan-3β-ol or a pharmaceutically acceptable salt thereof to said patient.

13. The method according to claim 10, wherein 5α-hydroxy-6β-[2-(1H-imidazol-4-yl)ethylamino]cholestan-3β-ol or a pharmaceutically acceptable salt thereof and the antineoplastic agent are simultaneously administered to said patient.

14. The method according to claim 10, wherein 5α-hydroxy-6β-[2-(1H-imidazol-4-yl)ethylamino]cholestan-3β-ol or a pharmaceutically acceptable salt thereof and the antineoplastic agent are sequentially administered to said patient.

15. The method according to claim 14, wherein 5α-hydroxy-6β-[2-(1H-imidazol-4-yl)ethylamino]cholestan-3β-ol or a pharmaceutically acceptable salt thereof is administered prior to the antineoplastic agent.

16. A method for restoring the sensibility of a tumor which is chemoresistant to an antineoplastic agent in a patient having a cancer selected from the group consisting of breast cancer, melanoma, lung cancer, embryonal carcinoma, neuroblastoma, glioma, colon cancer, and gastrointestinal cancer, consisting essentially of administering to said patient a therapeutically effective amount of 5α-hydroxy-6β-[2-(1H-imidazol-4-yl)ethylamino]cholestan-3β-ol or a pharmaceutically acceptable salt thereof and a therapeutically effective amount of said antineoplastic agent, wherein said antineoplastic agent is daunorubicine.

17. A method for increasing the sensibility of a tumor to an antineoplastic agent in a patient having a cancer selected from the group consisting of breast cancer, melanoma, lung cancer, embryonal carcinoma, neuroblastoma, glioma, colon cancer, and gastrointestinal cancer comprising administering to said patient 5α-hydroxy-6β-[2-(1H-imidazol-4-yl)ethylamino]cholestan-3β-ol or a pharmaceutically acceptable salt thereof in an amount sufficient to increase the sensibility of said tumor to said antineoplastic agent, wherein said antineoplastic agent is daunorubicine.

18. The method according to claim 17, wherein a dose of the antineoplastic agent is administered to said patient in combination with 5α-hydroxy-6β-[2-(1H-imidazol-4-yl)ethylamino]cholestan-3β-ol or a pharmaceutically acceptable salt thereof and said dose is lower than the dose of antineoplastic agent when not administered in combination with 5α-hydroxy-6β-[2-(1H-imidazol-4-yl)ethylamino]cholestan-3β-ol or a pharmaceutically acceptable salt thereof to said patient.

* * * * *